(12) United States Patent
Kosugi et al.

(10) Patent No.: US 10,557,819 B2
(45) Date of Patent: Feb. 11, 2020

(54) ELECTROLYTIC COPPER PLATING SOLUTION ANALYZER, AND ELECTROLYTIC COPPER PLATING SOLUTION ANALYSIS METHOD

(71) Applicant: TOPPAN PRINTING CO., LTD., Tokyo (JP)

(72) Inventors: Masahiro Kosugi, Tokyo (JP); Toshikazu Okubo, Tokyo (JP)

(73) Assignee: TOPPAN PRINTING CO., LTD., Tokyo (JP)

( * ) Notice: Subject to any disclaimer, the term of this patent is extended or adjusted under 35 U.S.C. 154(b) by 460 days.

(21) Appl. No.: 15/259,734

(22) Filed: Sep. 8, 2016

(65) Prior Publication Data

US 2016/0377573 A1 Dec. 29, 2016

Related U.S. Application Data

(63) Continuation of application No. PCT/JP2015/057164, filed on Mar. 11, 2015.

(30) Foreign Application Priority Data

Mar. 11, 2014 (JP) .................................. 2014-048161
Dec. 11, 2014 (JP) .................................. 2014-251155

(51) Int. Cl.
*G01N 27/42* (2006.01)
*G01N 27/416* (2006.01)
(Continued)

(52) U.S. Cl.
CPC ............. *G01N 27/423* (2013.01); *C25D 3/12* (2013.01); *C25D 3/22* (2013.01); *C25D 3/38* (2013.01);
(Continued)

(58) Field of Classification Search
CPC .. G01N 27/4161; G01N 27/42; G01N 27/423; C25D 3/12; C25D 3/22; C25D 3/38; C25D 3/58; C25D 21/12
(Continued)

(56) References Cited

U.S. PATENT DOCUMENTS 5,223,118 A 6/1993 Sonnenberg et al.
7,291,253 B2 11/2007 Pavlov et al.
(Continued)

OTHER PUBLICATIONS

Extended European Search Report dated Oct. 27, 2017 in corresponding application No. 15761848.9.
(Continued)

*Primary Examiner* — Edward J. Schmiedel
(74) *Attorney, Agent, or Firm* — Foley & Lardner LLP

(57) ABSTRACT

An electrolytic copper plating solution analyzer comprises an analysis container for accommodating a part of an electrolytic copper plating solution containing additives including a promoter, an inhibitor and a leveler, a working electrode immersed in the electrolytic copper plating solution accommodated in the analysis container, a reference electrode immersed in the electrolytic copper plating solution and used as a reference when a potential of the working electrode is determined, a counter electrode immersed in the electrolytic copper plating solution, a rotation drive unit for rotating the working electrode at a given speed, a current generation unit passing an electric current with a given current density between the working electrode and the counter electrode, a potential measurement unit for measuring the potential between the working electrode and the reference electrode, and an analysis unit for analyzing the relationship between an elapsed time after the current passage and the potential.

6 Claims, 3 Drawing Sheets

(51) Int. Cl.
　　　C25D 3/38　　　(2006.01)
　　　C25D 3/22　　　(2006.01)
　　　C25D 21/12　　(2006.01)
　　　C25D 3/58　　　(2006.01)
　　　C25D 3/12　　　(2006.01)
(52) U.S. Cl.
　　　CPC ............... *C25D 3/58* (2013.01); *C25D 21/12* (2013.01); *G01N 27/4161* (2013.01); *G01N 27/42* (2013.01)
(58) Field of Classification Search
　　　USPC .......... 205/81, 239, 271, 291, 305, 791, 794
　　　See application file for complete search history.

(56) References Cited

U.S. PATENT DOCUMENTS

| | | |
|---|---|---|
| 7,879,222 B2 | 2/2011 | Shalyt et al. |
| 8,440,555 B2 | 5/2013 | Okubo et al. |
| 2006/0183257 A1 | 8/2006 | Okubo et al. |

OTHER PUBLICATIONS

Toshikazu Okubu, Practical Methods to Monitor the Properties of Copper Plating Using Electrochemical Techniques, Cutting Edge and World Evaluation Technology, 2008, 857-862, vol. 59, No. 12.
International Search Report issued in International Patent Application No. PCT/JP2015/057164 dated May 12, 2015.

ELECTROLYTIC COPPER PLATING SOLUTION ANALYZER, AND ELECTROLYTIC COPPER PLATING SOLUTION ANALYSIS METHOD

CROSS-REFERENCE TO RELATED PATENT APPLICATIONS

This application is a continuation application filed under 35 U.S.C. § 111(a) claiming the benefit under 35 U.S.C. §§ 120 and 365(c) of International Application No. PCT/JP2015/057164 filed on Mar. 11, 2015, which is based upon and claims the benefit of priority of Japanese Patent Application No. 2014-048161, filed on Mar. 11, 2014, and Japanese Patent Application No. 2014-251155, filed on Dec. 11, 2014 the entire contents of which are all hereby incorporated by reference.

TECHNICAL FIELD

This invention relates to an electrolytic copper plating solution analyzer and also to a method for analyzing an electrolytic copper plating solution. More particularly, the invention relates to an electrolytic copper plating solution analyzer wherein an electrolytic copper plating solution is analyzed, which is used to deposit and grow an electrolytic copper plated film in a via hole (contact hole) or a through hole formed in high-density mounting boards, semiconductor substrates and semiconductor packaging boards thereby forming a contact electrode or through hole electrode (via) including the electrolytic copper plated film, and also to a method for analyzing an electrolytic copper plating solution.

BACKGROUND

An electrolytic copper plated film has been hitherto deposited and grown in a via hole (contact hole) or through hole (hereinafter referred to simply as "hole") formed in a high-density mounting board, a semiconductor substrate or a semiconductor packaging board thereby forming a via electrode (contact electrode) or a through-hole electrode including the electrolytic copper plated film.

In order to improve the physical properties and deposition properties of the plated film, additives having promotion action and inhibition action are added to the electrolytic copper plating solution.

As a promoter having the promotion action or a promotion effect (promotion function), SPS (bis(sodium sulfopropyl)disulfide) is used, for example.

Of additives showing the inhibition action or an inhibition effect, an additive having a strong inhibition action or strong inhibition effect and having a great influence on the formation of copper plating in a via hole is called an inhibitor, and an additive having a small inhibition action or small inhibition effect and capable of improving the smoothness of a copper plated surface is called a leveler.

The inhibitor used includes, for example, PEG (poly(ethylene glycol)).

The leveler used includes, for example, a polyamine.

To stabilize the quality of a plated film, importance is placed on the control and adjustment of the amounts of additives (concentrations of promoter, inhibitor and leveler) contained in the electrolytic copper plating solution. However, as time passes from a plating reaction initiation point, the additives undergo decomposition or property changes, and the control therefor is necessary.

For the control of additives, the usual practice is to use a CVS (Cyclic Voltammetry Stripping) method. With the CVS method, the potential of a platinum rotating disk electrode is repeatedly changed in a plating solution at a given speed, so that the deposition and dissolution of a metal plated film are caused to repeatedly occur on the electrode surface.

In the CVS method, the potential scanning speed is constant, so that the dissolution of the peak area of the voltammogram is proportional to an average deposition rate, which is in close relation with the concentration of an additive in a plating solution.

If the calibration curve of a standard plating solution is made, the CVS method enables the quantitative analysis of additives in a sample plating solution to be carried out.

With an existing CVS device using the CVS method, if additives undergo degradation due to the decomposition and property changes of the additives in an electrolytic copper plating solution although depending on the elapsed time from a plating reaction initiation point, then the analysis is made in terms of the concentrations of the additives including the quantities of the degraded additives.

As an analysis method wherein such additive degradation (i.e. decomposition and property changes of additives in the electrolytic copper plating solution) are taken into account, the technique described in PTL 1 is known.

In PTL 1, it is disclosed that the analysis of MPSA (3-mercaptopropylsulfonic acid), which is a decomposed matter of SPS added as a promoter, is made by use of the CVS method.

PTL 2 discloses the analysis of the decomposed matter of a leveler component by use of a voltammetric method.

However, although the analysis methods disclosed in PTLs 1 and 2 are feasible by the use of existing CVS devices, complicated operations are needed. More particularly, such operations are necessary to check potential variations by repeating potential scanning several times, or to measure two types of plating solutions provided at different dilution rates.

As a method of analyzing the influence of decomposed matters of additives contained in an electrolytic copper plating solution according to a method simpler than the methods of PTLs 1 and 2, techniques described in PTLs 3 and 4 are known.

In PTL 3, an analysis method of determining amounts of additives is disclosed by performing constant current electrolysis on an electrolytic copper plating solution containing a gloss agent and a leveler as additives to obtain a time-potential curve.

In PTL 4, an analysis method is disclosed wherein constant current electrolysis is performed on an electrolytic copper plating solution containing additives, and the state of the electrolytic copper plating solution is judged from the resulting time-potential curve.

In the case where the analysis methods of PTLs 3 and 4 are carried out, a rotating electrode is used.

CITATION LIST

Patent Literature

PTL 1: U.S. Pat. No. 7,291,253
PTL 2: U.S. Pat. No. 7,879,222
PTL 3: U.S. Pat. No. 5,223,118
PTL 4: U.S. Pat. No. 8,440,555

SUMMARY OF THE INVENTION

Technical Problem

However, with the analysis method disclosed in PTL 3, there is made no approach of obtaining parameters related to the electrode reaction of copper plating deposition based on the results obtained, and thus, quantitative analysis cannot be done.

The analysis method disclosed in PTL 4 is suitable for practical use in that the data are quantified approximately to the Boltzmann function. However, theoretical support is not enough, for which the parameters obtained by analyzing the results of the analysis do not always correctly show the electrode reaction of copper plating deposition on the basis of theory.

Therefore, with the analysis methods described in PTLs 3 and 4, a difficulty has been involved in figuring out the parameters, related to the electrode reaction of the copper plating deposition, as quantitative values based on theory.

It will be noted that the "parameters related to the electrode reaction of the copper plating deposition" used herein means those parameters, which are changed according to the balance of the effects of a promoter, an inhibitor and a leveler contained an electrolytic copper plating solution and show the features of the graphic profile obtained by measurement and which are quantitative values figuring out the states of the plating solution (e.g. the states of the promoter, inhibitor and leveler) from the graphic profile.

In other words, in the case where additives contained in an electrolytic copper plating solution and including, for example, a promoter, an inhibitor, and a leveler are adjusted by using the results obtained from the analysis methods set out in PTLs 3 and 4, the control of the additives cannot be made with a high degree of accuracy.

The present invention has been made to overcome such problems as set out above and contemplates to provide an electrolytic copper plating solution analyzer and a method for analyzing an electrolytic copper plating solution, wherein when the state of an electrolytic copper plating solution containing additives is controlled according to a constant current electrolytic method, more accurate, quantitative control can be ensured.

Improvement or Solution to Problem

A first embodiment of the invention is directed to an electrolytic copper plating solution analyzer, which comprises an analysis container for accommodating, as an analysis sample, a part of an electrolytic copper plating solution containing additives including a promoter, an inhibitor and a leveler, a working electrode that is immersed in the electrolytic copper plating solution accommodated in the analysis container and is capable of receiving and transferring electrons, a reference electrode immersed in the electrolytic copper plating solution accommodated in the analysis container and used as a reference when a potential of the working electrode is determined, a counter electrode immersed in the electrolytic copper plating solution accommodated in the analysis container, a rotation drive unit capable of rotating the working electrode at a given speed, a current generation unit capable of passing an electric current with a given current density between the working electrode and the counter electrode, a potential measurement unit for measuring a potential between the working electrode and the reference electrode, and an analysis unit for analyzing the relation between a time elapsed after the current passage and the potential, wherein when the relation between the elapsed time and the potential is analyzed, the analysis unit calculates parameters indicating a condition of the electrolytic copper plating solution based on such a reaction mechanism that a Cu(I) species generated on a surface of the working electrode during the course of the deposition reaction of a copper plated film is substituted for the inhibitor, which is located on the surface of the working electrode, as the deposition reaction of the copper plated film proceeds, the leveler is substituted for the Cu(I) species, which is located on the surface of the working electrode, as the deposition reaction of the copper plated film proceeds, and the Cu(I) species forms a complex at least with the promoter thereby showing a promotion function; and identifies the condition of the electrolytic copper plating solution by use of the parameters.

The promoter does not show any promotion function by itself, but acts to stabilize the chemically instable Cu(I) species by formation of a complex with the Cu(I) species. The chemically instable Cu(I) species shows a promotion function by formation of a complex at least with the promoter. For instance, the chemically instable Cu(I) species shows a promotion function by formation of complexes with a promoter, a decomposed matter of the promoter and a chloride.

It will be noted that the term "the condition of the electrolytic copper plating solution" used herein means a factor related to plating solution components that influence the physical properties and deposition properties of copper deposited on an object when the electrolytic copper plating solution is electrolyzed.

A second embodiment of the invention is directed to the electrolytic copper plating analyzer of the first embodiment wherein the analysis unit should preferably calculate, as parameters, $i_i$, $i_a$, $i_l$, $C_a^*/T_i$ and $k_2 \cdot C_l/T_i$ by analysis based on the following equations (1) to (4).

[Math. 1]

$$\eta = AT \cdot \ln\left[\frac{i_i}{I} \cdot \exp\left(-BI\frac{C_a^*}{T_i}t\right) + \frac{i_a}{I}\left\{1 - \exp\left(-BI\frac{C_a^*}{T_i}t\right)\right\} + \frac{i_l - i_a}{I} \cdot \exp\left(-\frac{k_2 C_l}{T_i}t\right)\right] \quad (1)$$

$$A = \frac{R}{\alpha F} \quad (2)$$

$$B = \frac{1}{nFd} \quad (3)$$

$$C_a^* = \frac{kC_a}{BI} \quad (4)$$

In the equations, $\eta$ is the potential indicated above, T is a given temperature indicated above, I is the current density, t is the elapsed time, $i_i$ is an exchange current density at the time of deposition reaction of the copper plated film in the presence of the inhibitor, $i_a$ is an exchange current density at the time of deposition reaction of the copper plated film in the presence of the Cu(I) species, $i_l$ is an exchange current density at the time of deposition reaction of the copper plated film in the presence of the leveler, $C_a$ is a concentration of the promoter in the solution bulk, $C_l$ is a concentration of the leveler in the solution bulk, $T_i$ is a saturation coverage of the inhibitor on the surface of the copper plated film, k is a reaction rate at which the inhibitor is substituted with the Cu(I) species with time due to the difference in adsorption rate therebetween, $k_2$ is a reaction rate at which the Cu(I) species is substituted with the leveler with time due to the difference in adsorption rate therebetween, R is a gas constant, α is a transfer coefficient, F is the Faraday constant, d is a molar density of copper, and n is the valance of copper.

A third embodiment of the invention is directed to an electrolytic copper plating solution analyzer, which comprises an analysis container for accommodating, as an analysis sample, a part of an electrolytic copper plating solution containing additives including a promoter, an inhibitor and a leveler, a working electrode that is immersed in the electrolytic copper plating solution accommodated in the analysis container and is capable of receiving and transferring electrons, a reference electrode immersed in the electrolytic copper plating solution accommodated in the analysis container and used as a reference when a potential of the working electrode is determined, a counter electrode immersed in the electrolytic copper plating solution accommodated in the analysis container, a rotation drive unit capable of rotating the working electrode at a given speed, a current generation unit capable of passing an electric current with a given current density between the working electrode and the counter electrode, a potential measurement unit for measuring a potential between the working electrode and the reference electrode, and an analysis unit for analyzing the relation between a time elapsed after the current passage and the potential, wherein when the relation between the elapsed time and the potential is analyzed, the analysis unit calculates parameters indicating a condition of the electrolytic copper plating solution based on such a reaction mechanism that a Cu(I) species generated on a surface of the working electrode during the course of the deposition reaction of a copper plated film is substituted for the inhibitor, which is located on the surface of the working electrode, as the deposition reaction of the copper plated film proceeds, the leveler is substituted for the inhibitor, which is located on the surface of the working electrode, as the deposition reaction of the copper plated film proceeds, and the Cu(I) species forms a complex at least with the promoter thereby showing a promotion function; and identifies the condition of the electrolytic copper plating solution by use of the parameters.

It will be noted that the promoter does not show any promotion function by itself, but acts to stabilize the chemically instable Cu(I) species by formation of a complex with the Cu(I) species. The chemically instable Cu(I) species shows a promotion function by formation of a complex at least with the promoter. For instance, the chemically instable Cu(I) species shows a promotion function by formation of complexes with a promoter, a decomposed matter of the promoter and a chloride.

A fourth embodiment of the invention is directed to the electrolytic copper plating solution analyzer of the third embodiment wherein the analysis unit should preferably analyze the relation between the elapsed time and the potential measured with the potential measurement unit based on the following equations (5) to (8) and calculate, as the parameters, $i_i$, $i_a$, $i_l$, $C_a^*/T_i$, and $k_3 \cdot C_l/T_i$.

[Math. 2]

$$\eta = AT \cdot \ln\left[\frac{i_i}{I} \cdot \exp\left(-BI\frac{C_a^*}{T_i}t\right) + \frac{i_a}{I}\left\{1 - \exp\left(-BI\frac{C_a^*}{T_i}t\right)\right\} + \frac{i_l - i_i}{I} \cdot \exp\left(-\frac{k_3 C_l}{T_i}t\right)\right] \quad (5)$$

$$A = \frac{R}{\alpha F} \quad (6)$$

$$B = \frac{1}{nFd} \quad (7)$$

$$C_a^* = \frac{kC_a}{BI} \quad (8)$$

In the equations, η is the potential indicated above, T is a given temperature indicated above, I is the current density, t is the elapsed time, $i_i$ is an exchange current density at the time of deposition reaction of the copper plated film in the presence of the inhibitor, $i_a$ is an exchange current density at the time of deposition reaction of the copper plated film in the presence of the Cu(I) species, $i_l$ is an exchange current density at the time of the deposition reaction of the copper plated film in the presence of the leveler, $C_a$ is a concentration of the promoter in the solution bulk, $C_l$ is a concentration of the leveler in the solution bulk, $T_i$ is a saturation coverage of the inhibitor on the surface of the copper plated film, k is a reaction rate at which the inhibitor is substituted with the Cu(I) species with time due to the difference in adsorption rate therebetween, $k_3$ is a reaction rate at which the inhibitor is substituted with the leveler with time due to the difference in adsorption rate therebetween, R is a gas constant, α is a transfer coefficient, F is the Faraday constant, d is a molar density of copper, and n is the valance of copper.

A fifth embodiment of the invention is directed to an electrolytic copper plating solution analyzer, which comprising an analysis container for accommodating, as an analysis sample, a part of an electrolytic copper plating solution containing additives serving as a promoter and an inhibitor, a working electrode that is immersed in the electrolytic copper plating solution accommodated in the analysis container and is capable of receiving and transferring electrons, a reference electrode immersed in the electrolytic copper plating solution accommodated in the analysis container and used as a reference when a potential of the working electrode is determined, a counter electrode immersed in the electrolytic copper plating solution accommodated in the analysis container, a rotation drive unit capable of rotating the working electrode at a given speed, a current generation unit capable of passing an electric current with a given current density between the working electrode and the counter electrode, a potential measurement unit for measuring a potential between the working electrode and the reference electrode, and an analysis unit for analyzing the relation between an elapsed time from the current passage and the potential, wherein when the relation between the elapsed time and the potential is analyzed, the analysis unit calculates parameters indicating a condition of the electrolytic copper plating solution based on such a reaction mechanism that a Cu(I) species generated on a surface of the working electrode during the course of the deposition reaction of a copper plated film is substituted for the inhibitor, which is located on the surface of the working electrode, as the deposition reaction of the copper plated film proceeds, and the Cu(I) species forms a complex at least with the promoter thereby showing a promotion function; and identifies the condition of the electrolytic copper plating solution by use of the parameters.

It will be noted that the promoter does not show any promotion function by itself, but acts to stabilize the chemically instable Cu(I) species by formation of a complex with the Cu(I) species. The chemically instable Cu(I) species shows a promotion function by formation of a complex at least with the promoter. For instance, the chemically instable Cu(I) species shows a promotion function by formation of complexes with a promoter, a decomposed matter of the promoter and a chloride.

A sixth embodiment of the invention is directed to the electrolytic copper plating solution analyzer of the fifth embodiment wherein the analysis unit should preferably analyze the relation between the elapsed time and the potential measured with the potential measurement unit based on the following equations (41) and (61) to (63) and calculate, as the parameters, $i_i$, $i_a$, and $C_a^*/T_i$.

[Math. 3]

$$\eta = A \cdot T \left[ \ln \left\{ \frac{i_i}{I} \exp\left(-B \cdot I \frac{C_a^*}{T_i} t\right) + \frac{i_a}{I} \left\{ 1 - \exp\left(-B \cdot I \frac{C_a^*}{T_i} t\right) \right\} \right\} \right] \quad (41)$$

$$A = \frac{R}{\alpha F} \quad (61)$$

$$B = \frac{1}{nFd} \quad (62)$$

$$C_a^* = \frac{kC_a}{BI} \quad (63)$$

In the equations, $\eta$ is the potential indicated above, T is a given temperature indicated above, I is the current density, t is the elapsed time, $i_i$ is an exchange current density at the time of deposition reaction of the copper plated film in the presence of the inhibitor, $i_a$ is an exchange current density at the time of deposition reaction of the copper plated film in the presence of the Cu(I) species, $C_a$ is a concentration of the promoter in the solution bulk, $T_i$ is a saturation coverage of the inhibitor on the surface of the copper plated film, k is a reaction rate at which the inhibitor is substituted with the Cu(I) species with time due to the difference in adsorption rate therebetween, R is a gas constant, $\alpha$ is a transfer coefficient, F is the Faraday constant, d is a molar density of copper, and n is the valance of copper.

A seventh embodiment of the invention is directed to the electrolytic copper plating solution analyzer of the fifth embodiment wherein the analysis unit should preferably analyze the relation between the elapsed time and the potential measured with the potential measurement unit based on the following equations (42) and (64) to (66) to calculate $i_a$ and $C_a^*/T_i$ as parameters.

[Math. 4]

$$\eta = A \cdot T \left[ \ln\left(\frac{i_a}{I}\right) + \ln\left\{ 1 - \exp\left(-B \cdot I \frac{C_a^*}{T_i} t\right) \right\} \right] \quad (42)$$

$$A = \frac{R}{\alpha F} \quad (64)$$

$$B = \frac{1}{nFd} \quad (65)$$

$$C_a^* = \frac{kC_a}{BI} \quad (66)$$

In the equations, $\eta$ is the potential indicated above, T is a given temperature indicated above, I is the current density, t is the elapsed time, $i_a$ is an exchange current density at the time of deposition reaction of the copper plated film in the presence of the Cu(I) species, $C_a$ is a concentration of the promoter in the solution bulk, $T_i$ is a saturation coverage of the inhibitor on the surface of the copper plated film, k is a reaction rate at which the inhibitor is substituted with the Cu(I) species with time due to the difference in adsorption rate therebetween, R is a gas constant, $\alpha$ is a transfer coefficient, F is the Faraday constant, d is a molar density of copper, and n is the valance of copper.

An eighth embodiment of the invention is directed to a method for identifying a condition of an electrolytic copper plating solution, which method comprising immersing a working electrode, a reference electrode and a counter electrode in an electrolytic copper plating solution that is kept at a given temperature and contains additives including a promoter, an inhibitor and a leveler, rotating the working electrode at a given speed, passing an electric current with a given current density between the working electrode and the counter electrode to measure a potential between the working electrode and the reference electrode, and analyzing the relation between a time elapsed from the current passage and the potential, wherein parameters indicating a condition of the electrolytic copper plating solution are calculated based on such a reaction mechanism that a Cu(I) species generated on a surface of the working electrode during the course of the deposition reaction of a copper plated film is substituted for the inhibitor, which is located on the surface of the working electrode, as the deposition reaction of the copper plated film proceeds, the leveler is substituted for the Cu(I) species, which is located on the surface of the working electrode, as the deposition reaction of the copper plated film proceeds, and the Cu(I) species forms a complex at least with the promoter thereby showing a promotion function thereby to identify the condition of the electrolytic copper plating solution by use of the parameters.

It will be noted that the promoter does not show any promotion function by itself, but acts to stabilize the chemically instable Cu(I) species by formation of a complex with the Cu(I) species. The chemically instable Cu(I) species shows a promotion function by formation of a complex at least with the promoter.

A ninth embodiment of the invention is directed to the method for analyzing an electrolytic copper plating solution of the eighth embodiment wherein when the analysis is made on the relation between the elapsed time after the passage of the current and the potential, the relation between the elapsed time and the potential should preferably be analyzed based on the following equations (1) to (4) to calculate $i_i$, $i_a$, $i_l$, $C_a^*/T_i$ and $k_2 \cdot C_l/T_i$ as the parameters.

[Math. 5]

$$\eta = AT \cdot \ln\left[ \frac{i_i}{I} \cdot \exp\left(-BI\frac{C_a^*}{T_i} t\right) + \right. \quad (1)$$

$$\left. \frac{i_a}{I}\left\{ 1 - \exp\left(-BI\frac{C_a^*}{T_i} t\right) \right\} + \frac{i_l - i_a}{I} \cdot \exp\left(-\frac{k_2 C_l}{T_i} t\right) \right]$$

$$A = \frac{R}{\alpha F} \quad (2)$$

$$B = \frac{1}{nFd} \quad (3)$$

$$C_a^* = \frac{kC_a}{BI} \quad (4)$$

In the equations, $\eta$ is the potential indicated above, T is a given temperature indicated above, I is the current density, t is the elapsed time, $i_i$ is an exchange current density at the time of deposition reaction of the copper plated film in the presence of the inhibitor, $i_a$—is an exchange current density at the time of deposition reaction of the copper plated film in the presence of the Cu(I) species, $i_l$ is an exchange current density at the time of deposition reaction of the copper plated film in the presence of the leveler, $C_a$ is a concentration of the promoter in the solution bulk, $C_l$ is a concentration of the leveler in the solution bulk, $T_i$ is a saturation coverage of the inhibitor on the surface of the copper plated film, k is a reaction rate at which the inhibitor is substituted with the Cu(I) species with time due to the difference in adsorption rate therebetween, $k_2$ is a reaction rate at which the Cu(I) species is substituted with the leveler with time due to the difference in adsorption rate therebetween, R is a gas constant, α is a transfer coefficient, F is the Faraday constant, d is a molar density of copper, and n is the valance of copper.

A tenth embodiment of the invention is directed to a method for analyzing an electrolytic copper plating solution, which method comprising immersing a working electrode, a reference electrode and a counter electrode in an electrolytic copper plating solution that is kept at a given temperature and contains additives including a promoter, an inhibitor and a leveler, rotating the working electrode at a given speed, passing an electric current with a given current density between the working electrode and the counter electrode to measure a potential between the working electrode and the reference electrode, and analyzing the relation between an elapsed time after the current passage and the potential, wherein parameters indicating a condition of the electrolytic copper plating solution are calculated based on such a reaction mechanism that a Cu(I) species generated on a surface of the working electrode during the course of the deposition reaction of a copper plated film is substituted for the inhibitor, which is located on the surface of the working electrode, as the deposition reaction of the copper plated film proceeds, the leveler is substituted for the inhibitor, which is located on the surface of the working electrode, as the deposition reaction of the copper plated film proceeds, and the Cu(I) species forms a complex at least with the promoter thereby showing a promotion function; and the condition of the electrolytic copper plating solution is identified by use of the parameters.

It will be noted that the promoter does not show any promotion function by itself, but acts to stabilize the chemically instable Cu(I) species by formation of a complex with the Cu(I) species. The chemically instable Cu(I) species shows a promotion function by formation of a complex at least with the promoter.

An eleventh embodiment of the invention is directed to the method for analyzing an electrolytic copper plating solution related to the tenth embodiment, wherein when the analysis is made on the relation between the time elapsed after the passage of the current and the potential, the relation between the elapsed time and the potential should preferably be analyzed based on the following equations (5) to (8) to calculate $i_i$, $i_a$, $i_l$, $C_a^*/T_i$ and $k_3 \cdot C_l/T_i$ as the parameters.

[Math. 6]

$$\eta = AT \cdot \ln\left[\frac{i_i}{I} \cdot \exp\left(-BI\frac{C_a^*}{T_i}t\right) + \frac{i_a}{I}\left\{1-\exp\left(-BI\frac{C_a^*}{T_i}t\right)\right\} + \frac{i_l - i_i}{I} \cdot \exp\left(-\frac{k_3 C_l}{T_i}t\right)\right] \quad (5)$$

$$A = \frac{R}{\alpha F} \quad (6)$$

$$B = \frac{1}{nFd} \quad (7)$$

$$C_a^* = \frac{kC_a}{BI} \quad (8)$$

In the equations, η is the potential indicated above, T is a given temperature indicated above, 1 is the current density, t is the elapsed time, $i_i$ is an exchange current density at the time of deposition reaction of the copper plated film in the presence of the inhibitor, $i_a$ is an exchange current density at the time of deposition reaction of the copper plated film in the presence of the Cu(I) species, $i_l$ is an exchange current density at the time of the deposition reaction of the copper plated film in the presence of the leveler, $C_a$ is a concentration of the promoter in the solution bulk, $C_l$ is a concentration of the leveler in the solution bulk, $T_i$ is a saturation coverage of the inhibitor on the surface of the copper plated film, k is a reaction rate at which the inhibitor is substituted with the Cu(I) species with time due to the difference in adsorption rate therebetween, $k_3$ is a reaction rate at which the inhibitor is substituted with the leveler with time due to the difference in adsorption rate therebetween, R is a gas constant, α is a transfer coefficient, F is the Faraday constant, d is a molar density of copper, and n is the valance of copper.

A twelfth embodiment of the invention is directed to an electrolytic copper plating solution analyzer, which comprising an analysis container for accommodating, as an analysis sample, a part of an electrolytic copper plating solution containing additives serving as a promoter and an inhibitor, a working electrode that is immersed in the electrolytic copper plating solution accommodated in the analysis container and is capable of receiving and transferring electrons, a reference electrode immersed in the electrolytic copper plating solution accommodated in the analysis container and used as a reference when a potential of the working electrode is determined, a counter electrode immersed in the electrolytic copper plating solution accommodated in the analysis container, a rotation drive unit capable of rotating the working electrode at a given speed, a current generation unit capable of passing an electric current with a given current density between the working electrode and the reference electrode, a potential measurement unit for measuring a potential between the working electrode and the reference electrode, and an analysis unit for analyzing the relation between a time elapsed from the current passage and the potential, wherein when the relation between the elapsed time and the potential is analyzed, parameters indicating a condition of the electrolytic copper plating solution are calculated based on such a reaction mechanism that a Cu(I) species generated on a surface of the working electrode during the course of the deposition reaction of a copper plated film is substituted for the inhibitor, which is located on the surface of the working electrode, as the deposition reaction of the copper plated film proceeds, and the Cu(I) species shows a promotion function; and identifies the condition of the electrolytic copper plating solution by use of the parameters.

It is to be noted that the term "condition of the electrolytic copper plating solution" means a factor expressing generic characteristics relating to a plating solution, which influence the physical properties and deposition properties of copper to be deposited on an object when an electrolytic copper plating solution is subjected to electrolysis.

According to the twelfth embodiment, when the relation between the elapsed time after current passage and the potential between the working electrode and the reference electrode is analyzed, the parameters related to the condition of a plating solution can be obtained based on the reaction mechanism that a Cu(I) species generated on the surface of the working electrode during the copper deposition reaction in the measurement is substituted for the initiator located on the surface of the working electrode as the deposition reaction of the copper plated film proceeds, and the Cu(I) species itself shows the promotion function.

The use of the resulting parameters enables, for example, the condition of an electrolytic copper plating solution being used in a plating apparatus to be controlled and kept, thereby stably maintaining the physical properties and deposition properties of plated film.

A thirteenth embodiment of the invention is directed to the electrolytic copper plating solution analyzer of the twelfth embodiment, wherein the relation between the elapsed time and the potential can be analyzed with the analysis unit according to the following equations (41) and (61) to (63) to calculate $i_i$, $i_a$ and $C_a^*/T_i$ as the parameters.

[Math. 7]

$$\eta = A \cdot T\left[\ln\left\{\frac{i_i}{I}\exp\left(-B \cdot I\frac{C_a^*}{T_i}t\right) + \frac{i_a}{I}\left\{1 - \exp\left(-B \cdot I\frac{C_a^*}{T_i}t\right)\right\}\right\}\right] \quad (41)$$

$$A = \frac{R}{\alpha F} \quad (61)$$

$$B = \frac{1}{nFd} \quad (62)$$

$$C_a^* = \frac{kC_a}{BI} \quad (63)$$

In the equations, η is the potential indicated above, T is a given temperature indicated above, I is the current density, t is the elapsed time, $i_i$ is an exchange current density at the time of deposition reaction of the copper plated film in the presence of the inhibitor, $i_a$ is an exchange current density at the time of deposition reaction of the copper plated film in the presence of the Cu(I) species, $C_a$ is a concentration of the promoter in the solution bulk, $T_i$ is a saturation coverage of the inhibitor on the surface of the copper plated film, k is a reaction rate at which the inhibitor is substituted with the Cu(I) species with time due to the difference in adsorption rate therebetween, R is a gas constant, α is a transfer coefficient, F is the Faraday constant, d is a molar density of copper, and n is the valance of copper.

According to the thirteenth embodiment of the invention, since the relation between the time elapsed from the current passage and the potential is analyzed by use of the equation (41), parameters necessary for identifying the condition of an electrolytic copper plating solution can be accurately obtained.

A fourteenth embodiment of the invention is directed to the electrolytic copper plating analyzer of the twelfth embodiment, wherein when the analysis is made on the relation between the elapsed time after the current passage and the potential, the relation between the elapsed time and the potential can be analyzed based on the following equations (42) and (64) to (66) to calculate $i_a$ and $C_a^*/T_i$ as the parameters.

[Math. 8]

$$\eta = A \cdot T\left[\ln\left(\frac{i_a}{I}\right) + \ln\left\{1 - \exp\left(-B \cdot I\frac{C_a^*}{T_i}t\right)\right\}\right] \quad (42)$$

$$A = \frac{R}{\alpha F} \quad (64)$$

$$B = \frac{1}{nFd} \quad (65)$$

$$C_a^* = \frac{kC_a}{BI} \quad (66)$$

In the equations, η is the potential indicated above, T is a given temperature indicated above, I is the current density, t is the elapsed time, $i_a$ is an exchange current density at the time of deposition reaction of the copper plated film in the presence of the Cu(I) species, $C_a$ is a concentration of the promoter in the solution bulk, $T_i$ is a saturation coverage of the inhibitor on the surface of the copper plated film, k is a reaction rate at which the inhibitor is substituted with the Cu(I) species with time due to the difference in adsorption rate therebetween, R is a gas constant, α is a transfer coefficient, F is the Faraday constant, d is a molar density of copper, and n is the valance of copper.

According to the fourteenth embodiment, since the relation between the elapsed time and the potential is analyzed using the equation (42), the analysis can be made more simply than in the case using the equation (41).

Advantageous Effects of Invention

According to the above embodiments of the invention, when the potential between the working electrode and the reference electrode, both immersed in analysis sample of an electrolytic copper plating solution, is measured to analyze the relation between an elapsed time and the potential, parameters indicating a condition of the electrolytic copper plating solution are calculated based on such a reaction mechanism that a Cu(I) species or an inhibitor is replaced with a leveler as the deposition reaction of a copper plated film proceeds, and the Cu(I) species forms a complex at least with a promoter to show a promotion function. Therefore, when the condition of the electrolytic copper plating solution containing additives is controlled by use of a constant current electrolytic technique, more accurate quantitative control becomes possible.

It should be noted that on this occasion, the inhibitor is substituted with the Cu(I) species, or the inhibitor is substituted with the Cu(I), which is then further substituted with the leveler, or the inhibitor is substituted with the Cu(I) species and the inhibitor is further substituted with leveler.

DESCRIPTION OF REPRESENTATIVE EMBODIMENTS

Figure 1:
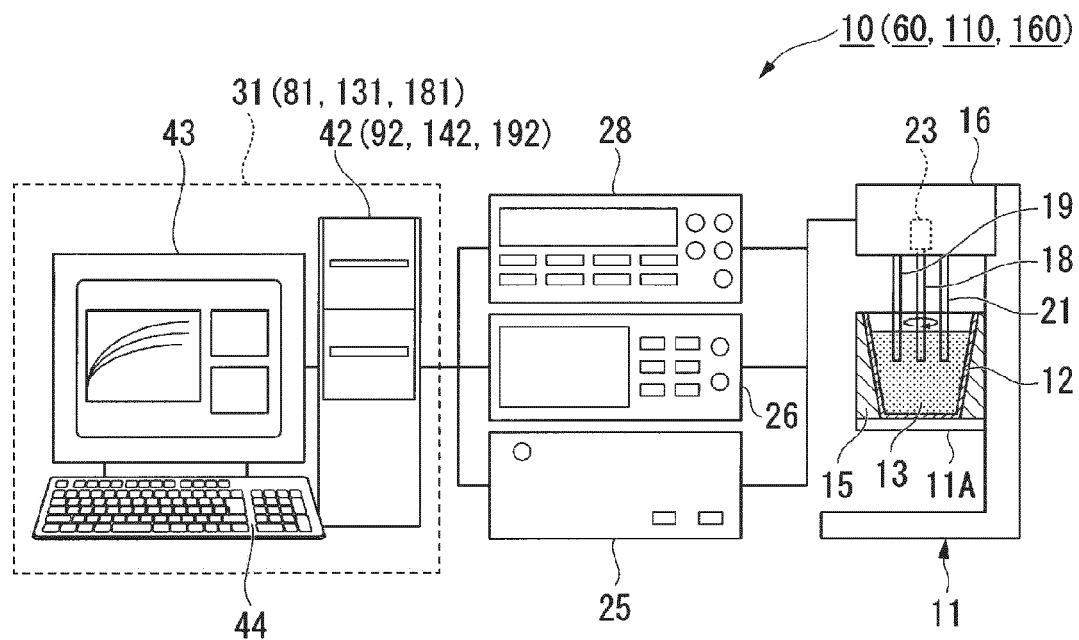
FIG. 1 is a schematic view showing an example of a configuration of an electrolytic copper plating solution analyzer according to an embodiment of the invention.

The embodiments of the invention are now described with reference to the accompanying drawings. In all the drawings and even in different embodiments, like members are indicated by like or corresponding reference numerals, and duplicate illustration therefor is omitted.

The drawings used in the following description are those for merely illustrating the configurations of the embodiments of the invention, and the size, thickness and dimension of the respective parts shown may sometimes differ from those of an actual electrolytic copper plating solution analyzer. The embodiments described below are simply representative of the invention and the invention should not necessarily be limited thereto.

First Embodiment

An electrolytic copper plating solution analyzer according to a first embodiment of the invention is now described.

Figure 2:
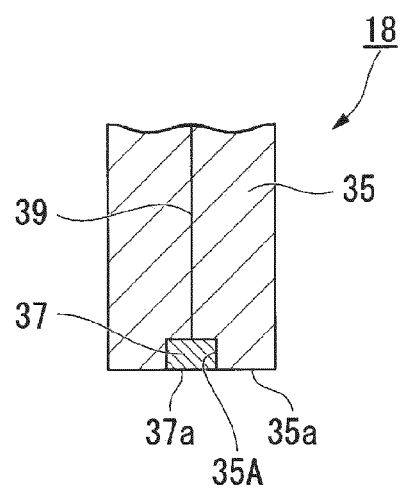
FIG. 2 is a view showing an example of a tip portion of a working electrode used in the electrolytic copper plating solution analyzer according to the embodiment of the invention.

FIG. 1 is a schematic view showing an example of a configuration of an electrolytic copper plating solution analyzer of the first embodiment of the invention. FIG. 2 is a view showing an example of a tip portion of a working electrode used in the electrolytic copper plating solution analyzer of the first embodiment of the invention.

As shown in FIG. 1, an electrolytic copper plating solution analyzer 10 of the present embodiment includes a stand 11, an analysis container 12, a temperature holding unit 15, an electrode support 16, a working electrode 18, a reference electrode 19, a counter electrode 21, a rotation drive unit 23, a current generation unit 26, a potential measurement unit 28, a controller 25 and an analysis unit 31.

The stand 11 has a stage portion 11A mounting the analysis container 12 and the temperature holding unit 15 thereon.

The analysis container 12 is one wherein part of an electrolytic copper plating solution 13 serving as an analysis object is accommodated as an analysis sample. The analysis container 12 is disposed on the stage portion 11A of the stand 11.

The electrolytic copper plating solution 13 used as an analysis object includes, for example, an electrolytic copper plating solution 13 having been used in an appropriate plating apparatus, not shown. In this regard, however, the analysis object should not be limited to the used electrolytic copper plating solution 13, but a fresh electrolytic copper plating solution 13 may be analyzed, for example, for the purpose of obtaining comparative data in the case of good condition.

The electrolytic copper plating solution 13 is then illustrated.

The electrolytic copper plating solution 13 can contain, at least, a Cu (II) ion and an additive.

The additive is a mixture of components showing the actions of a promoter, an inhibitor and a leveler. Although these components may be frequently added as separate compounds serving as a promoter, an inhibitor and a leveler, a compound having a plurality of functional groups and showing a plurality of actions may be used.

Usable promoters include, for example, sulfur-containing compounds such as SPS [bis(sodium sulfopropyl)disulfide] and the like.

Usable inhibitors include, for example, water-soluble polymers such as polyethylene oxide, polypropylene oxide and the like, PEG [poly(ethylene glycol)] and the like.

Usable levelers include, for example, organic compounds such as a polyamine, a polyacrylamine, poly(N-methyldiallylamine), poly(N-vinylpyrrolidone), poly(N-vinyl-N'-methylimidazolium chloride) and the like.

The above additives contained in the electrolytic copper plating solution 13 are supplied from a number of suppliers singly or in combination thereof.

The electrolytic copper plating solution 13 may further contain an anion (e.g. a sulfate ion) serving as a counter ion to the Cu (II) ion, an acid (e.g. sulfuric acid), or a chlorine ion.

The amount of the Cu (II) ion contained in the electrolytic copper plating solution 13 can be set, for example, within a range of 2 g/liter to 70 g/liter. The amount of sulfuric acid can be set, for example, within a range of 10 g/liter to 200 g/liter. The amount of the chloride is appropriately within a range of 1 mg/liter to 150 mg/liter.

The optimum amounts of the respective additives can be determined after the performance evaluation of the electrolytic copper plating solution 13. The optimum concentrations of additive components can be as well.

The temperature holding unit 15 is disposed on the stage portion 11A so as to surround the analysis container 12 along the outer side periphery thereof. The temperature holding unit 15 holds the temperature of the electrolytic copper plating solution 13 accommodated in the analysis container 12 at a given level.

The temperature of the electrolytic copper plating solution 13 is preferably selected from the range of 20° C. to 35° C., for example. The temperature variation that would be within an acceptable range is ±1° C.

The temperature holding unit 15 used includes, for example, a thermostatic water bath.

The use of such a temperature holding unit 15 enables the analytical accuracy to be stabilized.

It should be noted that although the temperature holding unit 15 surrounding the outer side periphery of the analysis container 12 is shown in FIG. 1 by way of example, the temperature holding unit 15 may be so configured as to cover not only the outer side periphery of the analysis container 12, but also the bottom face of the analysis container 12.

The electrode support 16 is fixed at an upper end portion of the stand 11. The electrode support 16 is disposed in face-to-face relation with the liquid surface of the electrolytic copper plating solution 13 accommodated in the analysis container 12.

The electrode support 16 is a member supporting the working electrode 18, the reference electrode 19 and the counter electrode 21, appearing hereinafter, at the back end thereof.

In this embodiment, the potential measured by use of the working electrode 18, reference electrode 19 and counter electrode 21 varies depending on the positional relation among the working electrode 18, reference electrode 19 and counter electrode 21.

Accordingly, it is preferred that the measurement of the potential should be performed under such conditions that the positions of the working electrode 18, reference electrode 19 and counter electrode 21 are invariably fixed. For instance, it is not preferred that the positional relationship among the working electrode 18, reference electrode 19 and counter electrode 21 has to be adjusted whenever an electrolytic copper plating solution 13 (analysis sample) is changed with another one.

In order to obtain more reproducible potential data, it is preferred to adopt, as the electrode support 16, such a configuration that the positional relationship among the working electrode 18, reference electrode 19 and counter electrode 21 can be fixed.

The working electrode 18 is supported with the electrode support 16 through the rotation drive unit 23, appearing hereinafter, so as to permit the tip end portion of the working electrode 18 to be immersed in the electrolytic copper plating solution 13.

The working electrode 18 is one that allows electron acceptance and transfer with a chemical species in the electrolytic copper plating solution 13.

As shown in FIG. 2, the working electrode 18 has an exterior member 35, a working electrode body 37 and a conductive wire 39.

The exterior member 35 is provided as a columnar insulating member.

The exterior member 35 is formed with a flat tip end face 35a at the tip end portion thereof. At the center of the tip end face 35a, there is formed a working electrode body accommodation portion 35A in the form of a recess accommodating the working electrode body 37.

The working electrode body 37 is formed of a conductive material and is accommodated in the working electrode body accommodation portion 35A.

The working electrode body 37 has a surface 37a exposed from the exterior member 35. Hence, when the working electrode body 37 is immersed in the electrolytic copper plating solution 13, the working electrode body 37 is able to contact the electrolytic copper plating solution 13 at the surface 37a.

As to the shape of the working electrode body 37, a disk-shaped electrode is preferred, for example, although not limited thereto.

The surface area of the surface 37a is preferably set, for example, within a range of 0.01 cm$^2$ to 1 cm$^2$.

The material of the working electrode body 37 includes, for example, a noble metal material such as electrically stable platinum or the like.

It will be noted that the exterior member 35, working electrode body 37 and surface 37a are not limited to those shapes mentioned above or shown in the figures.

The conductive wire 39 is connected at one end thereof with the working electrode body 37 and is also electrically connected to the current generation unit 26.

As shown in FIG. 1, the reference electrode 19 is so supported with the electrode support 16 that the tip end portion of the reference electrode 19 is immersed in the electrolytic copper plating solution 13.

The reference electrode 19 is an electrode used as a reference for determining the potential of the working electrode 18.

The material of the reference electrode 19 includes, for example, saturated calomel ($Hg/Hg_2Cl_2$), silver/silver chloride (Ag/AgCl) or the like.

The counter electrode 21 is so supported with the electrode support 16 that the tip end portion of the counter electrode 21 is immersed in the electrolytic copper plating solution 13.

The counter electrode 21 is one that causes a reaction at the interface between the electrode and the electrolytic copper plating solution 13 by passing an electric current between the counter electrode 21 and the working electrode 18 through the electrolytic copper plating solution 13.

The counter electrode 21 includes, for example, a copper electrode that is a consumable electrode, a platinum-coated titanium electrode that is a hardly consumable electrode, or the like.

In order not to allow all electric currents to be subject to rate limiting with the reaction on this electrode, the surface area of the counter electrode 21 is preferably such that the surface area immersible in the electrolytic copper plating solution 13 is not less than the surface area of the surface 37a of the working electrode body 37 of the working electrode 18. In particular, the surface area of the counter electrode 21 immersible in the electrolytic copper plating solution 13 is preferably from 1 time to 50 times the surface area 37a of the working electrode body, for example.

The counter electrode 21 may also be called counter electrode or auxiliary electrode.

The rotation drive unit 23 is accommodated in the electrode support 16 and connected to the working electrode 18 at the back end thereof.

The rotation drive unit 23 is a device unit, with which the working electrode 18 is rotated at a given speed.

The number of rotations (rotation speed) of the working electrode 18 with the rotation drive unit 23 can be set, for example, within a range of 10 rpm to 8000 rpm.

When the number of rotations of the working electrode 18 with the drive rotation unit 23 is changed, the diffusion state of the additives in the electrolytic copper plating solution 13 is changed. Hence, the ease in occurrence of a difference in potential measurement data, appearing hereinafter, varies depending on the differences in concentration among the respective components of the additives according to the magnitude of rotation.

Accordingly, the number of rotations, at which the variation of measurement data is relatively liable to appear depending on the formulation of the respective components of the additive, has been confirmed beforehand according to the preliminary study wherein a test of changing the number of rotations is carried out. The measurement of potential, appearing hereinafter, is performed by use of this number of rotations.

The number of rotations of the working electrode 18 with the rotation drive unit 23 is preferably not less than 10 rpm, at which the effect of rotation appears. On the other hand, if the number of rotations of the working electrode 18 with the rotation drive unit 23 is larger than 8000 rpm, the mechanical control of the rotation number becomes unfavorably difficult.

The current generation unit 26 is electrically connected to the working electrode 18 and the counter electrode 21, respectively.

The current generation unit 26 is a device unit of passing, between the working electrode 18 and the counter electrode 21, an electric current with a given current density I in the working electrode 18.

The current generation unit 26 is preferably made, for example, of a material which enables a DC current of 10 A or below and 10V or below to be controllable within a range of not larger than ±10 mV or below relative to a set voltage and also within a range of not larger than ±10 mA relative to a set current.

The current generation unit 26 includes, for example, a DC stabilized power supply.

The current density I in the working electrode 18 is preferably within a range of 0.1 A/dm² to 20 A/dm², more preferably 0.5 A/dm² to 5 A/dm².

If the current density I is less than 0.1 A/dm², a difference in the results of potential measurement is less likely to appear. If the current density I is larger than 5 A/dm², the potential is less likely to be stabilized.

The potential measurement unit 28 is communicationally connected to the working electrode 18, the reference electrode 19 and an analysis unit 31 appearing hereinafter.

The potential measurement unit 28 is a device unit of measuring a potential η between the working electrode 18 and the reference electrode 19 while passing a current with a given current density I between the working electrode 18 and the counter electrode 21. The data relating to the potential η measured with the potential measurement unit 28 is transmitted to the analysis unit 31.

As the potential measurement unit 28, there can be used, for example, a potentiometer, a voltmeter, a multimeter and the like, wherein the measurement is possible within a potential accuracy of about ±10 mV when the potential is measured.

It will be noted that prior to commencement of the measurement of the potential the working electrode 18 has to be rotated at a given rotation speed.

The measurement time of the potential η (hereinafter referred to as "measurement time $t_m$") should preferably be made as short as possible within a range where the value of the potential η becomes stable.

If the measurement time $t_m$ is too short to be, for example, 10 seconds or below, the copper plated film deposited on the surface 37a of the working electrode 18 is not stabilized, making it difficult to obtain reliable parameters.

The measurement time $t_m$ is preferably appropriately set within a range, for example, of 1 minute to 40 minutes.

The controller 25 is communicationally connected to the rotation drive unit 23, current generation unit 26 and potential measurement unit 28 and controls these units.

It will be noted that as shown in FIG. 1, the controller 25, current generation unit 26 and potential measurement unit 28 may be formed as separate members, or the plurality of units may be formed integrally.

Additionally, the controller 25 may be formed integrally with the analysis unit 31 appearing hereinafter.

The analysis unit 31 has an analysis unit body 42, a display 43 displaying the results of analysis, a keyboard 44 and a mouse (not shown). As a device configuration of the analysis unit 31, there can be used a computer, e.g. a personal computer, including CPU, a memory, input and output interfaces, an external memory device and the like.

The analysis unit body 42 is communicationally connected to the controller 25, current generation unit 26, potential measurement unit 28, display 43, keyboard 44 and mouse (not shown).

The analysis unit body 42 may be communicationally connected to the rotation drive unit 23 so as to allow the rotation speed of the working electrode 18 to be controlled.

The analysis unit body 42 stores a program for controlling the controller 25, current generation unit 26, potential measurement unit 28 and display 43 and a program for carrying out a method of analyzing an electrolytic copper plating solution described hereinafter.

The analysis unit body 42 enables a number of controls and data analyses by executing these programs.

For example, an instance of the data analyses made with the analysis unit body 42 includes those analysis data wherein parameters indicating a condition of the electrolytic copper plating solution 13 based on the data of the potential η measured with the potential measurement unit 28 and identify the condition of the electrolytic copper plating solution 13 by using the calculated parameters.

The analysis unit body 42 should preferably control overall functions relating from the measurement to the analysis of the potential η and have the function of controlling a series of measurements and analyses.

In the case where the analysis unit body 42 is communicationally connected to the rotation drive unit 23, a program for controlling the rotation drive unit 23 may be stored in the analysis unit body 42.

The details of the control and data analyses conducted with the analysis unit 31 are described along with the operative illustration of the electrolytic copper plating solution analyzer 10.

Next, the operations of the electrolytic copper plating solution analyzer 10 of the present embodiment are described centered around a method for analyzing an electrolytic copper plating solution of the embodiment.

In order to identify the condition of an electrolytic copper plating solution 13 used in an appropriate plating device (not shown) by means of the electrolytic copper plating solution analyzer 10, a preparation step, a potential measurement step and an analysis step in a method for analyzing an electrolytic copper plating solution according to this embodiment are carried out in this order.

The preparation step is one wherein the working electrode 18, reference electrode 19 and counter electrode 21 are immersed in the electrolytic copper plating solution 13 kept at a given temperature, and the working electrode 18 is rotated at a given speed.

More particularly, the electrolytic copper plating solution 13 is accommodated in the analysis container 12 and held with the temperature holding unit 15. Next, the working electrode 18, reference electrode 19 and counter electrode 21 are immersed in the electrolytic copper plating solution 13.

When the temperature of the electrolytic copper plating solution 13 reaches a given temperature T, the controller 25 is operated so as to cause the rotation drive unit 23 to be rotated at a rotation speed predetermined for analysis. This permits the working electrode 18 supported with the rotation drive unit 23 to start rotation at a given rotation speed.

It is to be noted that in the case where the analysis unit body 42 of the analysis unit 31 is able to control the rotation drive unit 23, the above operation can be performed through the analysis unit body 42.

In this way, the preparation step has been completed.

Next, the potential measurement step is performed. This step is one wherein a current whose current density I is made constant is passed between the working electrode 18 and the counter electrode 21 to measure a potential between the working electrode 18 and the reference electrode 19.

In this step, the potential measurement is commenced by operating a keyboard 44 or a mouse to start a data analysis program by using the analysis unit body 42.

As a consequence, a control signal is fed from the analysis unit body 42 to the current generation unit 26 and the potential measurement unit 28, so that the current generation unit 26 and the potential measurement unit 28 are operated to start the potential measurement. Alternatively, a control signal may be fed from the analysis unit body 42 via the controller 25 to the current generation unit 26 and the potential measurement unit 28, and the current generation unit 26 and the potential measurement unit 28 are operated to start the potential measurement.

That is, an electric current with a given current density I is passed from the current generation unit 26 between the working electrode 18 and the counter electrode 21, and the potential η is measured with the potential measurement unit 28.

The potential η is measured at appropriate measuring intervals during a predetermined measurement time $t_m$, and the measurement data of the potential η relative to the elapsed time t from the commencement of the current passage are obtained.

The resulting potential η in every elapsed time t is fed to the analysis unit 31.

The analysis unit 31 works in such a way that upon receipt of the measurement data of the potential η, the graph of the measurement data are displayed on a display 43.

Thus, the potential measurement step has been completed.

Next, the analysis step is carried out. This step is one wherein the relation between the time t elapsed from the commencement of the current being passed between the working electrode 18 and the counter electrode 21 and the potential η is analyzed.

This step is automatically started with the analysis unit 31 as soon as all the measurement data, which have been measured with the potential measurement unit 28 during the measurement time $t_m$, are fed to the analysis unit 31 after the lapse of the measurement time $t_m$.

The time variation of the potential η indicates the progress on the deposition reaction of a copper plated film in the electrolytic copper plating solution 13, which reflects a variation with time of the promotion effect (promotion function) and inhibition effect (inhibition function) of the deposition reaction due to the additives in the electrolytic copper plating solution 13.

Accordingly, if a factor indicating the promotion effect of the deposition reaction and a factor indicating the inhibition effect thereof can be obtained, for example, as quantitative parameters in view of the timewise variation of the potential η, it can be possible to identity the condition of the electrolytic copper plating solution 13.

With the electrolytic copper plating solution analyzer 10, the effects of the respective components (promoter, inhibitor and leveler) of the plating solution are quantified in terms of parameters ($i_i$, $i_a$, $i_l$, $C_a$*/T and $k_2 \cdot C_l/T_l$), thus enabling the condition of the plating solution to be identified.

In order to calculate the parameters indicating the condition of the electrolytic copper plating solution 13 from the timewise variation of the potential η, the present inventors have derived the theoretical relational equation including, as constant coefficients, parameters of a factor indicating the promotion effect of the deposition reaction and a factor indicating the inhibition effect based on the reaction mechanism of the deposition reaction. The thus-derived relational equation is applied to the timewise variation of the potential η, thus arriving at the identification of the parameters.

On this occasion, prior to the illustration of the operation of the analysis unit 31, the reaction mechanism and relational equation used in the analysis step of the present embodiment carried out with the analysis unit 31 are illustrated.

Initially, the deposition mechanism of a copper plated film, which the present inventors have found out, is illustrated.

The electrolytic copper plating solution 13 contains a Cu (II) ion, an additive made of a mixture of components showing the actions of an inhibitor, a promoter and a leveler, an anion (e.g. sulfate ion) that is a counter ion of the Cu (II) ion, an acid (e.g. sulfuric acid) and a chlorine ion.

In this regard, however, the promoter does not show any promotion effect when used singly, but acts to stabilize a chemically instable Cu(I) species by formation of a complex with the Cu(I) species generated on the surface 37a of the working electrode body 37 shown in FIG. 2. The chemically instable Cu(I) species shows a promotion effect by formation of a complex at least with the promoter. For instance, the chemically instable Cu(I) species shows a promotion effect by formation of complexes with the promoter, the decomposed matter of the promoter, and a chloride.

Immediately after commencement of the deposition of a copper plated film on a negative electrode (cathode electrode) by electrolysis, an inhibitor, a promoter and a leveler used as additives are adsorbed on the negative electrode to cover the surface of the copper plated film.

The copper plated film is deposited between the additive thin film adsorbed on the surface of the negative electrode and the negative electrode and is taken up as a metal film. It will be noted that immediately after commencement of the deposition of the copper plated film, the degree of adsorption effect of the additives decreases in the order of inhibitor, promoter and leveler.

The reduction reaction of the Cu (II) ion into metallic copper (i.e. zero-valent Cu) proceeds through a Cu(I) ion intermediate. Although most of the Cu(I) ion is reduced into metallic copper, part of the Cu(I) ion forms, as a side product, a Cu(I) species by binding with the chloride and the promoter component and is stabilized, part of which remains on the deposited metallic copper surface.

Accordingly, as the deposition reaction of the copper plated film proceeds, the surface concentration of the Cu(I) species on the copper plated film surface increases. The Cu(I) species includes, for example, a Cu(I) complex formed, for example, from the Cu(I) ion generated by reaction between the promoter component in the electrolytic copper plating solution 13 and the electrode. The Cu(I) complex has the catalytic action of the electrode reaction and thus the promotion effect appears.

Further, as the deposition reaction of the copper plated film proceeds, the concentration of the Cu(I) species (e.g. Cu(I) complex) in the vicinity of the surface of the negative electrode increases, under which shortly after commencement of the deposition of the copper plated film, the Cu(I) species is substituted for the inhibitor adsorbed on the negative electrode. During the course of the deposition of the copper plated film, the leveler is substituted for the Cu(I) species adsorbed on the negative electrode.

In the deposition of the copper plated film, the inhibitor component, the leveler component and a promoter component, which does not form a complex with the Cu(I) ion, are supplied from the electrolytic copper plating solution 13 on the surface of the negative electrode. On the other hand, the inhibitor component, leveler component and promoter component existing on the surface of the negative electrode are desorbed. The balance of the additive components on the negative electrode surface moves toward equilibrium by the action of these formation, adsorption and desorption.

According to Reference 2 described later, the Cu(I) species in the reaction mechanism that the complex of the Cu(I)

species on the negative electrode surface shows a promotion effect includes not only the Cu(I) species formed on and attached to the negative surface as described above, but also the Cu(I) species desorbed from the negative electrode after the formation on the negative electrode surface and the Cu(I) species formed in the electrolytic copper plating solution.

It is supposed that such Cu(I) species, not existing on the negative electrode surface, shows a promotion effect different from that of the Cu(I) species on the negative electrode surface. When the Cu(I) species not existing on the negative electrode surface moves toward the negative electrode surface by diffusion, it takes part in the copper plating deposition reaction on the negative electrode and shows a promotion effect.

The reaction mechanism of the deposition reaction set out above is now applied to the reaction in the analysis container 12 of the electrolytic copper plating solution analyzer 10. In the course of the copper deposition reaction at the time of measurement of potential η, the Cu(I) species generated on the surface 37a of the working electrode 18 serving as a negative electrode is substituted for the inhibitor on the surface 37a as the deposition reaction proceeds. Moreover, the leveler is substituted for the Cu(I) species thereby providing such a reaction mechanism that the Cu(I) species forms a complex at least with the promoter to show a promotion effect. For example, the Cu(I) species shows a promotion effect by formation of complexes with a promoter, a decomposed matter of the promoter and a chloride.

As the relational equations expressing the timewise change of potential η in the reaction mechanism, the following equations (1) to (4) are adopted in the present embodiment.

[Math. 9]

$$\eta = AT \cdot \ln\left[\frac{i_i}{I} \cdot \exp\left(-BI\frac{C_a^*}{T_i}t\right) + \frac{i_a}{I}\left\{1 - \exp\left(-BI\frac{C_a^*}{T_i}t\right)\right\} + \frac{i_l - i_a}{I} \cdot \exp\left(-\frac{k_2 C_l}{T_i}t\right)\right] \quad (1)$$

$$A = \frac{R}{\alpha F} \quad (2)$$

$$B = \frac{1}{nFd} \quad (3)$$

$$C_a^* = \frac{kC_a}{BI} \quad (4)$$

In the equations, exp represents an exponential function, ln represents a natural logarithmic function, η is a potential, T is a temperature of the electrolytic copper plating solution 13, I is a current density, t is an elapsed time, $i_i$ is an exchange current density at the time of the deposition reaction of a copper plated film in the presence of an inhibitor, $i_a$ is an exchange current density at the time of the deposition reaction of a copper plated film in the presence of a Cu(I) species, $i_l$ is an exchange current density at the time of the deposition reaction of a copper plated film in the presence of a leveler, $C_a$ is a concentration of a promoter in a solution bulk, $C_l$ is a concentration of a leveler in the solution bulk, $T_i$ is a saturation coverage of the inhibitor on the surface of the copper plated film, k is a reaction rate at which the inhibitor is substituted with the Cu(I) species with time due to the difference in adsorption rate therebetween, $k_2$ is a reaction rate at which the Cu(I) species is substituted with the leveler with time due to the difference in adsorption rate therebetween, R is a gas constant, α is a transfer coefficient, F is the Faraday constant, d is a molar density of copper, and n is the valance of copper.

It will be noted that the exchange current densities $i_i$, $i_a$ and $i_l$ are, respectively, those exchange current densities on the surface 37a of the working electrode 18.

Next, how to obtain the equations (1) to (4) is described.

The wiring formation on a semiconductor substrate by use of an electrolytic copper plating method is a widely spread technique, and much discussion has been made on the action of inhibitor and promoter on a plating surface in a great number of reports.

For example, in "Mechanistic Analysis of the Bottom-up Fill in Copper Interconnect Metallization" (Rohan Akolkar and Uziel Landau)—described in D351-D359 of 156(9) of Journal of The Electrochemical Society (2009) (hereinafter referred to as Reference 1), in order to simulate the filling properties of a copper plated film by bottom-up deposition in a via hole and a trench formed in a semiconductor substrate, there are described the results of analyses of diffusion and adsorption behaviors of additives made of an inhibitor and a promoter.

Further, in "Practical Methods to Monitor the Properties of Copper Plating Using Electrochemical Techniques" described in the Journal of the Surface Finishing Society of Japan, Vol. 59, No. 12, 2008, p 857 to p 862, (hereinafter referred to as Reference 2), it is described that a Cu(I) complex, which is a reaction product of a promoter and Cu(I), shows a promotion effect in an electrolytic copper plating solution.

In the above references, it is assumed that the inhibitor is slower in diffusion than the promoter and is higher in adsorption, and in contrast, the promoter is higher in diffusion and slower in adsorption.

In the references, the local deposition rate of a copper plated film is simulated in view of the adsorption behaviors of an inhibitor component and a promoter component on the inner and outer surfaces of a via hole.

On this occasion, the deposition rates of the copper plated film on the inner and outer surfaces of the via hole are obtained as an entire current is distributed in response to the adsorption behaviors of the additive components on the electrode surface, i.e. the coverages of the inhibitor and promoter.

Furthermore, it is assumed in the references that the diffusion and adsorption rates differ between the inhibitor and the promoter, so that the promoter is substituted with the once adsorbed inhibitor as time passes. This is a way of interpreting such a mechanism that bottom-up deposition occurs by preferential adsorption of the promoter on the bottom surface of the via hole.

The thoughts of these references relating to the promoter and inhibitor can also be applied to the phenomenon that occurs on the surface 37a of the rotating working electrode 18 in the present embodiment.

In this regard, however, with the present embodiment, there is no need of consideration of an area not covered with any of the inhibitor and promoter.

In the embodiment, since the rotating working electrode 18 is used, supply of the additive components contained in the electrolytic copper plating solution 13 to the electrode surface is adequate, so that no consideration for the difference in diffusion rate is necessary.

According to the Tafel equation that is a fundamental electrochemical equation, current $I_i$ in a region of the surface 37a occupied with an inhibitor is represented by the following equation (9), current $I_a$ in a region of the surface 37a occupied with a promoter is represented by the following equation (10), and current $I_l$ in a region of the surface 37a occupied with a leveler is represented by the following equation (11).

[Math. 10]

$$I_i = i_i \theta_i \exp\left[-\frac{\alpha_i F}{RT}\eta\right] \quad (9)$$

$$I_a = i_a \theta_a \exp\left[-\frac{\alpha_a F}{RT}\eta\right] \quad (10)$$

$$I_l = i_l \theta_l \exp\left[-\frac{\alpha_l F}{RT}\eta\right] \quad (11)$$

In the equations, $\alpha_i$ is a transfer coefficient of an inhibitor, $\alpha_a$ is a transfer coefficient of a promoter, $\alpha_l$ is a transfer coefficient of a lever, $\theta_i$ is a coverage of the inhibitor on the surface 37a, $\theta_a$ is a coverage of the promoter on the surface 37a, and $\theta_l$ is a coverage of the leveler on the surface 37a.

Since the current density I on the surface 37a is a sum of the current densities $I_i$, $I_a$ and $I_l$, the current density I can be expressed by the following equation (12).

[Math. 11]

$$I = i_i \theta_i \exp\left[-\frac{\alpha_i F}{RT}\eta\right] + i_a \theta_a \exp\left[-\frac{\alpha_a F}{RT}\eta\right] + i_l \theta_l \exp\left[-\frac{\alpha_l F}{RT}\eta\right] \quad (12)$$

The transfer coefficients $\alpha_i$, $\alpha_a$ and $\alpha_l$ are approximately equal to one another. Such a copper plating reaction is a reversible reaction, so that the transfer coefficients $\alpha_i$, $\alpha_a$ and $\alpha_l$ are considered to be all approximately at 0.5. Hence, the transfer coefficients $\alpha_i$, $\alpha_a$ and $\alpha_l$ can be substituted with a transfer coefficient $\alpha$.

When using the transfer coefficient $\alpha$, the following equations (13) and (14) can be obtained from the above equation (12).

[Math. 12]

$$I = (i_i \theta_i + i_a \theta_a + i_l \theta_l) \exp\left[-\frac{\alpha F}{RT}\eta\right] \quad (13)$$

$$\eta = \frac{RT}{\alpha F} \times \ln\frac{i_i \theta_i + i_a \theta_a + i_l \theta_l}{I} \quad (14)$$

As to the changes of the coverages $\theta_i$, $\theta_a$ and $\theta_l$ the inhibitor is adsorbed on the surface 37a at the initial stage of the deposition of the copper plated film on the surface 37a based on such a reaching mechanism of the embodiment as stated above. The adsorbed inhibitor is substituted with the promoter as time passes, and the promoter adsorbed on the surface 37a is substituted with the leveler.

Since the coverage $\theta_a$ of the promoter is changed to the coverage $\theta_l$ of the leveler, the coverage of the promoter added with an amount of the promoter substituted with the leveler (i.e. a sum of the coverages $\theta_a$ and $\theta_l$) is taken as $\theta_a'$.

The coverages $\theta_i$ and $\theta_l$ can be expressed by the following equations (15) and (16) based on the diffusion formula according to the model of the above references.

[Math. 13]

$$\theta_i = \exp\left[-\frac{1}{T_i}kC_a t\right] \quad (15)$$

$$\theta_l = \exp\left[-\frac{1}{T}k_2 C_l t\right] \quad (16)$$

Since the total of the coverages $\theta_i$ and $\theta_a'$ is at "1". The coverage $\theta_a'$ can be expressed by the following equation (17).

[Math. 14]

$$\theta_a' = 1 - \theta_i \quad (17)$$

Since the coverage $\theta_a'$ is the sum of the coverages $\theta_a$ and $\theta_l$, the coverage $\theta_a$ can be expressed by the following equation (18).

[Math. 15]

$$\theta_a = \theta_a' - \theta_l \quad (18)$$

When the above equations (15) to (18) are substituted into the equation (14), the following equation (19) is obtained.

[Math. 16]

$$\eta = \frac{RT}{\alpha F} \cdot \ln\left[\frac{i_i}{I} \cdot \exp\left(-\frac{1}{T_i}kC_a t\right) + \frac{i_a}{I}\left\{1 - \exp\left(-\frac{1}{T_i}kC_a t\right)\right\} + \frac{i_l - i_a}{I} \cdot \exp\left(-\frac{1}{T_i}k_2 C_l t\right)\right] \quad (19)$$

With the case of containing an inhibitor, a promoter and a leveler, the above equation (19) is a relational equation showing the timewise change of the potential $\eta$, which is derived based on such a model that the inhibitor adsorbed on the surface 37a is substituted with the promoter as time passes and the promoter adsorbed on the surface 37a is substituted with the leveler as time passes, both depending the difference in adsorption rate of the respective components.

However, it has been found that there is a great difference between an actually measured potential and the potential $\eta$ calculated from the above equation (19).

As a result of extensive studies, it has been found that it might be better to assume other reaction mechanism than to consider that the promoter is brought by diffusion from the electrolytic copper plating solution 13.

More particularly, the Cu(I) species generated on the surface 37a of the working electrode 18 is substituted for the inhibitor on the surface 37a of the working electrode 18 and the leveler is substituted for the Cu(I) species on the surface 37a of the working electrode 18 in the course of the deposition reaction of the copper plated film as the deposition reaction of the copper deposited film proceeds. Moreover, the Cu(I) species forms a complex at least with the promoter to show a promotion effect. Where such a reaction mechanism as set out above is supposed to work, the results of the measurement could be better interpretable.

Consideration is taken to such a reaction mechanism that the Cu(I) species generated on the negative electrode surface according to the copper deposition reaction is substituted for the inhibitor on the negative electrode surface as the deposition reaction proceeds and the Cu(I) species itself forms a complex at least with the promoter to show a promotion effect, under which k of the above equation (19) is substituted with a factor including a current density. In other words, we have considered that the Cu(I) species to be reacted increases in amount, or the reaction rate increases, in proportion to the current density.

Accordingly, in the equation (1), the reaction rate k in the above equation (19) is replaced by a factor including the current density I as shown in the following equation (20).

[Math. 17]

$$k = \frac{BC_a^*}{C_a} I \qquad (20)$$

At the current density I, the Cu(I) generated in the course of the copper reduction reaction on the promoter of a solution bulk having a concentration of $C_a$, and a freshly generated Cu(I) species is substituted for an inhibitor layer existing on the electrode surface. In this connection, the Cu(I) species are not present singly and show different promotion effects, respectively. However, because it is substantially impossible to obtain the concentrations of the respective types of Cu(I) species, the factor $C_a^*$ showing the promotion effect of the Cu(I) species as a whole and including the concentration $C_a$ is defined and is used as a parameter obtained from measurement. This may be considered as $C_a$ multiplied by a coefficient indicating a degree of promotion.

The coefficient B is a coefficient introduced for adjusting a dimension and is expressed by the above equation (3).

Since the Cu(I) species has a plurality of formulations having different promotion effects, it is substantially impossible to obtain the concentrations of the respective formulations.

However, the promotion effect factor $C_a^*$ is proportional to the concentration $C_a$ of the promoter in the solution bulk and is a factor indicating the promotion effect of the Cu(I) species as a whole. In other words, while taking the decomposition and the alteration of properties of the additives into account, the promotion effect factor is a value indicating the total of the promotion effects in the electrolytic copper plating solution 13.

Next, the operations of the analysis unit 31 making use of the above equation (1) in the analysis step is illustrated.

In the present embodiment, an analysis program for calculating the parameters of the equation (1) is memorized in the analysis unit body 42. The analysis program calculates parameters by applying measured data of the potential η transmitted from the potential measurement unit 28 to the above equation (1).

The analysis method used in the analysis program is not specifically limited. For instance, there may be adopted analytical methods using a curve fitting by use of a least-squares technique, an inclination of measured potentials and an average value of measured potentials.

In this embodiment, a curve fitting method using the least-squares technique is adopted in one instance.

The constants used for the analysis, e.g. constants necessary for the calculation of the equations (2) and (3), have been preliminarily memorized in the analysis unit body 42.

When the analysis program of the analysis unit body 42 is executed, $p_1$, $p_2$, $p_3$, $p_4$ and $p_5$ expressed by the following equations (21) to (25) (which may be sometimes abbreviated as parameters $p_1$ to $p_5$) are calculated as parameters.

In the present embodiment, since the least-squares technique is used, the analysis unit body 42 works in such a way that appropriate initial values are set as the parameters $p_1$ to $p_5$, under which when the analysis program is executed, calculation is repeated while changing the parameters until a deviation from the measured data is converged to minimum in the least-squares technique. In this embodiment, the sum of squared residuals S are also calculated.

[Math. 18]

$$p_1 = i_i \qquad (21)$$

$$p_2 = i_a \qquad (22)$$

$$p_3 = i_l \qquad (23)$$

$$p_4 = \frac{C_a^*}{T_i} \qquad (24)$$

$$p_5 = \frac{k_2 C_l}{T_i} \qquad (25)$$

The thus calculated parameters $p_1$ to $p_5$, the function η(t) determined by the curve fitting, and the sum of squared residuals S are displayed on the display 43 along with the graph of the measured data.

These parameters $p_1$ to $p_5$ are those parameters, from which the condition of the electrolytic copper plating solution 13, i.e. the states of the inhibitor, Cu(I) species and leveler, can be known.

Hence, the combinations of the parameters $p_1$ to $p_5$ are a group of numerical values identifying the condition of the electrolytic copper plating solution 13.

The parameters $p_1$, $p_2$ and $p_3$ are, respectively, exchange current densities $i_i$, $i_a$ and $i_l$. When the respective effects of the inhibitor, Cu(I) species and leveler increase, the magnitudes of the exchange current densities $i_i$, $i_a$ and $i_l$ are changed.

The parameter $p_4$ expressed by $C_a^*/T_i$ is a parameter indicating a ratio between the promotion effect and the inhibition effect.

It will be seen that if the parameter $p_4$ increases, the promotion effect increases relatively to the inhibition effect. It will also been seen that if the parameter $p_4$ decreases, the inhibition effect increases relatively to the promotion effect.

The parameter $p_5$ expressed by $k_2 \cdot C_l/T_i$ is a parameter indicating the relationships among the substitution reaction rate between the Cu(I) species and the leveler, the smoothing effect and the inhibition effect.

When the parameter $p_5$ increases, the smoothing effect increases. When the parameter $p_5$ decreases, the smoothing effect decreases. If the parameter $p_5$ is outside a certain range, the respective effects become excessive, leading to the occurrence of some failure.

For example, with via fill plating, such a phenomenon appears that the degree of filling of plated copper in the via hole lowers.

Whether or not the condition of the electrolytic copper plating solution 13 identified with these parameters $p_1$ to $p_5$ is good can be judged when judgment conditions are preset like the first embodiment.

The judgment conditions can be set, for example, in such a way that samples applied with these parameters of the electrolytic copper plating solution 13 are used to conduct a performance evaluation test for use as a plating solution, after which the judgment conditions can be set based on the correspondence between the values of the respective parameters and the results of the evaluation.

For the judgment conditions, for example, it is possible to determine the acceptable ranges of the respective parameters, within which a good performance is obtained.

It is also possible not to determine the acceptable range of every parameter, but to determine the acceptable ranges based on the combinations of plural parameters or the values of weighed evaluation formulas.

Such a judgment may be made by a measurer while checking the respective parameters displayed on the display 43. Alternatively, the judgment conditions may be memorized in the analysis unit body 42, followed by automatic judgment with the analysis unit body 42 by comparison between the values of the respective parameters and the judgment conditions. In the case where the judgment is made with the analysis unit body 42, the results of the judgment are displayed on the display 43 along with the values of the respective parameters.

In the present embodiment, the sum S of squared residuals is also calculated, and the accuracy of the curve fitting can be judged depending on the magnitude of the sum S of squared residuals. If the sum S of squared residual is too large, an influence of a measurement error, such as too large a variation of measurement data of the potential η, should be taken into account, for example. In this case, although depending on the magnitude of the sum S of squared residual, some measures may be taken: the measurement of the potential is done again; or the analysis is made again after removal of apparently abnormal data.

According to the electrolytic copper plating solution analyzer 10 of the present embodiment, the potential η between the working electrode 18 and the reference electrode 19, both immersed in an analysis sample of the electrolytic copper plating solution 13, is measured, and the relation between an elapsed time t and the potential η is analyzed, thereby enabling parameters indicating the condition of the electrolytic copper plating solution 13 to be calculated.

In the course of the analysis, the parameters expressing the condition of the electrolytic copper plating solution 13 can be obtained based on such a reaction mechanism: the Cu(I) species generated on the surface 37a of the working electrode 18 during the deposition reaction of a copper plated film is substituted for an inhibitor located on the surface 37a as the deposition reaction of the copper plated film proceeds; and a leveler is substituted for the Cu(I) species located on the surface 37a as the deposition reaction of the copper plated film proceeds, with the result that the Cu(I) species shows a promotion effect by formation of a complex at least with a promoter. The parameters identified in this way are calculated based on the model of the reaction mechanism in the deposition reaction represented by the foregoing equation (1), so that the condition of the electrolytic copper plating solution 13 can be identified accurately and quantitatively.

When the condition of the electrolytic copper plating solution 13 used in a plating apparatus (not shown) is controlled and maintained by use of the thus obtained parameters, the physical properties and deposition properties of the plated copper can be stably held.

Second Embodiment

An electrolytic copper plating solution analyzer of a second embodiment of the present invention is illustrated.

As shown in FIG. 1, an electrolytic copper plating solution analyzer 60 of the present embodiment is provided with an analysis unit 81 in place of the analysis unit 31 of the electrolytic copper plating solution analyzer 10 of the first embodiment.

The analysis unit 81 is provided with an analysis unit body 92 in place of the analysis unit body 42 of the analysis unit 31.

The description below is centered around a difference from the first embodiment.

The analysis unit body 92 differs from the first embodiment in that the measurement data of potential η are analyzed by using the following equations (5) to (8) instead of the foregoing equations (1) to (4).

It will be noted that the equations (6), (7) and (8) are similar to the equations (2), (3) and (4) in the first embodiment. Among the constants and variables used in the respective equations, those common to the first embodiment are not illustrated again.

[Math. 19]

$$\eta = AT \cdot \ln\left[\frac{i_i}{I} \cdot \exp\left(-BI\frac{C_a^*}{T_i}t\right) + \frac{i_a}{I}\left\{1 - \exp\left(-BI\frac{C_a^*}{T_i}t\right)\right\} + \frac{i_l - i_a}{I} \cdot \exp\left(-\frac{k_3 C_l}{T_i}t\right)\right] \quad (5)$$

$$A = \frac{R}{\alpha F} \quad (6)$$

$$B = \frac{I}{nFd} \quad (7)$$

$$C_a^* = \frac{kC_a}{BI} \quad (8)$$

In the equations, $k_3$ is a reaction rate, at which an inhibitor is substituted with a leveler with time due to the difference in adsorption rate.

The equation (5) is one that represents a timewise change of the potential η in the case where a reaction mechanism different from the first embodiment is assumed as a reaction mechanism of the deposition reaction in the electrolytic copper plating solution 13.

In connection with the equation (5), the deposition reaction mechanism of plated copper, which we have found, is described.

When an electric current is applied to the electrolytic copper plating solution 13, a copper plated film starts to be deposited on a negative electrode (cathode electrode) by electrolysis and immediately thereafter, additives including an inhibitor, a promoter and a leveler are adsorbed on the negative electrode to cover the surface of the copper plated film.

The copper plated film is deposited between the additive thin film layer adsorbed on the negative electrode surface and the surface of the negative electrode and is incorporated as a metal film. It will be noted that immediately after the commencement of deposition of the copper plated film, the degree of adsorption effect of the additives decreases in the order of inhibitor, promoter and leveler.

The reduction reaction of the Cu (II) ion to metallic copper (i.e. zero valent Cu) goes through the formation of a Cu(I) ion serving as an intermediate. Although most of the Cu(I) is reduced to metallic copper, part thereof binds with a chloride or a promoter component to form Cu(I) species as a side product and is stabilized, part of which remains on the surface of the deposited metallic copper.

Accordingly, as the deposition reaction of the copper plated film proceeds, the surface concentration of the Cu(I) species on the surface of the copper plated film increases. This Cu(I) species corresponds, for example, to a Cu(I) complex formed from the Cu(I) ion generated by the reaction between the promoter component in the electrolytic copper plating solution 13 and the electrode, and the complex has the catalytic action on the electrode reaction, for which a promotion effect appears.

Further, as the deposition reaction of the copper plated film proceeds, the Cu(I) species (e.g. Cu(I) complex) in the vicinity of the surface of the negative electrode increases in concentration. Immediately after the commencement of deposition of the copper plated film, the Cu(I) species is substituted for the inhibitor adsorbed on the negative electrode. During the course of the deposition of the copper plated film, the leveler is substituted for the inhibitor adsorbed on the negative electrode.

In the deposition of the copper plated film, an inhibitor component, a leveler component and a promoter component, which does not form a complex with the Cu(I) ion, are supplied on the surface of the negative electrode from the electrolytic copper plating solution 13 along with the Cu (II) ion. On the other hand, the inhibitor component, the leveler component and the promoter component existing on the surface of the negative electrode are desorbed. The balance of the additive components on the electrode surface moves to equilibrium due to these behaviors of formation, adsorption and desorption.

According to the reference 2, in the reaction mechanism that the Cu(I) species complex on the surface of the negative electrode shows a promotion effect, the Cu(I) species includes, aside from the Cu(I) species formed on and attached to the negative electrode surface as described above, the Cu(I) species once formed on the negative electrode surface and subsequently desorbed from the negative electrode and the Cu(I) species formed in the electrolytic copper plating solution 13 (e.g. on the surface of an anode electrode in the electrolytic copper plating solution 13).

Such Cu(I) species not present on the negative electrode surface is considered to show a promotion effect (promotion function) different from the Cu(I) species on the surface of the negative electrode. When the Cu(I) species not present on the negative electrode surface moves to the surface of the negative electrode by diffusion, it takes part in the copper deposition reaction at the negative electrode and shows a promotion effect.

When the deposition reaction mechanism described above is applied to the reaction in the analysis container 12 of the electrolytic copper plating solution analyzer 60, a reaction mechanism proceeds as follows: a Cu(I) species generated on the surface 37a of the working electrode 18 serving as a negative electrode is substituted for an inhibitor on the surface 37a in the course of the copper deposition reaction at the time of the measurement of the potential η as the deposition reaction proceeds; and a leveler is substituted for the inhibitor, and this Cu(I) species forms a complex at least with a promoter to show a promotion effect (promotion function).

It will be noted that the promoter does not show any promotion effect by itself, but acts to stabilize the chemically instable Cu(I) species by formation of a complex with the Cu(I) species. The chemically instable Cu(I) species shows a promotion effect by formation of a complex at least with the promoter. For example, the chemically instable Cu(I) species shows a promotion effect by formation of complexes with a promoter, the decomposed matter of the promoter and a chloride.

How to obtain the above equations (5) to (8) is illustrated with respect to differences from the equations (1) to (4) in the first embodiment.

As stated in the first embodiment, the equations (13) and (14) are established with respect to the current density I and potential η for the deposition reaction in the electrolytic copper plating solution 13.

As to the variations of the coverages $\theta_i$, $\theta_a$ and $\theta_l$, the inhibitor is adsorbed on the surface 37a at an initial stage of the deposition of a copper plated film on the surface 37a based on the reaction mechanism of the present embodiment. However, it is considered that the thus adsorbed inhibitor is substituted with a promoter as time passes, and the inhibitor adsorbed on the surface 37a is substituted with a leveler.

Since the coverage $\theta_i$ of the inhibitor is replaced by the coverages $\theta_a$, $\theta_l$ of the promoter and leveler, the coverage of the inhibitor, to which a fraction replaced with the leveler is added (i.e. the sum of $\theta_i$ and $\theta_l$), is taken as $\theta_i'$. The coverage $\theta_i'$ is a coverage of the inhibitor prior to the replacement with the promoter.

The coverages $\theta_i'$ and $\theta_l$ can be expressed, according to the model of the foregoing reference, by the following equations (26), (27) based on the diffusion.

[Math. 20]

$$\theta_i' = \exp\left[-\frac{1}{T_i}kC_a t\right] \quad (26)$$

$$\theta_l = \exp\left[-\frac{1}{T_i}k_3 C_l t\right] \quad (27)$$

Since the total of the coverages and $\theta_i'$ is 1, the coverage $\theta_a$ can be expressed by the following equation (28).

[Math. 21]

$$\theta_a = 1 - \theta_i' \quad (28)$$

Since the coverage $\theta_i'$ is the sum of the coverages $\theta_i$ and $\theta_l$, the coverage $\theta_i$ can be expressed by the following equation (29).

[Math. 22]

$$\theta_i = \theta_i' - \theta_l \quad (29)$$

When the equations (26) to (29) are substituted into the equation (14), the following equation (30) is obtained.

[Math. 23]

$$\eta = \frac{RT}{\alpha F} \cdot \ln\left[\frac{i_i}{I} \cdot \exp\left(-\frac{1}{T_i}kC_a t\right) + \frac{i_a}{I}\left\{1 - \exp\left(-\frac{1}{T_i}kC_a t\right)\right\} + \frac{i_l - i_i}{I} \cdot \exp\left(-\frac{1}{T_i}k_3 C_l t\right)\right] \quad (30)$$

In the case where an inhibitor, a promoter and a leveler are contained, the above equation (30) is a relational equation indicating a timewise change of the potential η based on the model that the inhibitor adsorbed on the surface 37a is substituted with the promoter with time and the inhibitor adsorbed on the surface 37a is substituted with the leveler with time, both depending on the adsorption rates of the respective components.

However, we have found that there is a great difference between the potential obtained with an actual measurement and the potential η calculated by the above equation (30).

As a result of extensive studies, it has been found that it might be better to presume other reaction mechanism than to consider that the promoter is brought by diffusion from the electrolytic copper plating solution 13.

For example, when such a reaction mechanism is supposed that the Cu(I) species generated on the surface 37a of the working electrode 18 is substituted for the inhibitor on the surface 37a of the working electrode in the course of the deposition reaction of a copper plated film as the deposition reaction of the copper plated film proceeds, and the leveler is substituted for the inhibitor on the surface 37a of the working electrode 18 thereby enabling the Cu(I) species to show a promotion effect, the results of the measurement could be better understood.

Accordingly, in the equation (5), the reaction rate k of the equation (30) is replaced by a factor including the current density I as shown in the equation (20) like the first embodiment.

Next, the operation of the electrolytic copper plating solution analyzer 60 of the embodiment is described centered around a method for analyzing an electrolytic copper plating solution according to the present embodiment.

In order to identify the condition of the electrolytic copper plating solution 13 used in an appropriate plating apparatus (not shown) by means of the electrolytic copper plating solution analyzer 60, a preparation step, a potential measurement step and an analysis step in the analysis method of an electrolytic copper plating solution of the embodiment are conducted in this order.

The preparation step and the potential measurement step of the embodiment are the same as the preparation and potential measurement steps of the first embodiment except that the electrolytic copper plating solution analyzer 60 is used.

Next, the analysis step of the embodiment is carried out. The difference from the first embodiment resides in that the analysis step is carried out by using an analysis unit 81 instead of the analysis unit 31.

This step is automatically initiated with the analysis unit 81 when, after a lapse of measurement time $t_m$, all measurement data measured with the potential measurement unit 28 during the measurement time $t_m$ are transmitted to the analysis unit 81.

In this embodiment, an analysis program calculating parameters in the equation (5) is memorized in an analysis unit body 92. The analysis program allows the measurement data of the potential η transmitted from the potential measurement unit 28 to be applied to the equation (5) thereby calculating parameters.

With the electrolytic copper plating solution analyzer, the effects of the respective components (a promoter, an inhibitor and a leveler) in the plating solution are quantified in terms of parameters ($i_i$, $i_a$, $i_l$, $C_a^*/T_i$ and $k_3 \cdot C_l/T_i$), thus enabling the condition of the plating solution to be identified.

The analysis method used for the analysis program is not specifically limited. For instance, there can be adopts analysis methods such as a curve fitting using a least-square technique, an inclination of measured potentials, and an average value of measured potentials.

The constants used for the analysis, e.g. the constants necessary for the calculation of the equations (6), (7), have been memorized in the analysis unit body 92 beforehand.

When the analysis program of the analysis unit body 92 is executed, $p_{11}$, $p_{12}$, $p_{13}$, $p_{14}$ and $p_{15}$ (which may be sometimes abbreviated as parameters $p_{11}$ to $p_{15}$) expressed by the equations (31) to (35) are calculated as parameters.

In this embodiment, because of the use of least-square technique, the analysis unit body 92 sets appropriate initial values for the parameters $p_{11}$ to $p_{15}$, under which when the analysis program is executed, calculation is repeated while changing the parameters $p_{11}$ to $p_{15}$ until a deviation from the measured data is converged to minimum. In this embodiment, the sum of squared residuals S is also calculated.

[Math. 24]

$$p_{11} = i_i \tag{31}$$

$$p_{12} = i_a \tag{32}$$

$$p_{13} = i_l \tag{33}$$

$$p_{14} = \frac{C_a^*}{T_i} \tag{34}$$

$$p_{15} = \frac{k_3 C_l}{T_i} \tag{35}$$

The thus calculated parameters $p_{11}$ to $p_{15}$, the function η(t) determined by the curve fitting, and the sum of squared residuals S are displayed on the display screen 43 along with the graph of the measured data.

These parameters $p_{11}$ to $p_{15}$ are those parameters, from which the condition of the electrolytic copper plating solution 13, i.e. the states of the inhibitor, Cu(I) species and leveler, can be known.

Hence, the combinations of the parameters $p_{11}$ to $p_{15}$ are a group of numerical values identifying the condition of the electrolytic copper plating solution 13.

The parameters $p_{11}$, $p_{12}$ and $p_{13}$, respectively, correspond to exchange current densities $i_i$, $i_a$ and $i_l$. When the respective effects of the inhibitor, Cu(I) species and leveler increase, the magnitudes of the exchange current densities $i_i$, $i_a$ and $i_l$ are changed.

The parameter $p_{14}$ expressed by $C_a^*/T_i$ is a parameter indicating a ratio between the promotion effect and the inhibition effect.

It will be seen that if the parameter $p_{14}$ increases, the promotion effect increases relatively to the inhibition effect. It will also been seen that if the parameter $p_{14}$ decreases, the inhibition effect increases relatively to the promotion effect.

The parameter $p_{15}$ expressed by $k_3 \cdot C_l/T_i$ is a parameter representing the relationships among the substitution reaction rates of the promoter and the leveler, the smoothing effect and the inhibition effect.

When the parameter $p_{15}$ increases, the smoothing effect increases. When the parameter $p_{15}$ decreases, the smoothing effect decreases. If the parameter $p_{15}$ is outside a certain range, the respective effects become excessive, leading to the occurrence of a failure.

For example, with via fill plating, such a phenomenon appears that the degree of filling of plated copper in the via hole lowers.

Whether or not the condition of the electrolytic copper plating solution 13 identified with these parameters $p_{11}$ to $p_{15}$ is good can be judged when judgment conditions are preset like the first embodiment.

Such a judgment may be made by a measurer while checking the respective parameters displayed on the display 43. Alternatively, the judgment conditions may be memorized in the analysis unit body 92, followed by automatic judgment with the analysis unit body 92 by comparison between the values of the respective parameters and the judgment conditions. In the case where the judgment is made with the analysis unit body 92, the results of the judgment are displayed on the display 43 along with the values of the respective parameters.

In this way, the analysis step is completed.

According to the electrolytic copper plating solution analyzer 60 of the present embodiment, parameters expressing the condition of the electrolytic copper plating solution 13 can be calculated by measuring a potential η between the working electrode 18 and the reference electrode 19, both immersed in an analysis sample of the electrolytic copper plating solution 13, and analyzing the relation between an elapsed time t and the potential η.

In the course of carrying out the above analysis, the parameters expressing the condition of the electrolytic copper plating solution 13 can be obtained based on the following reaction mechanism: the Cu(I) species generated on the surface 37a of the working electrode 18 during the deposition reaction of a copper plated film is substituted for an inhibitor located on the surface 37a as the deposition reaction of the copper plated film proceeds; and a leveler is substituted for the inhibitor located on the surface 37a therewith as the deposition reaction of the copper plated film further proceeds, under which the Cu(I) specie forms a complex at least with a promoter and shows a promotion effect.

The parameters identified in this way are calculated based on the model of the reaction mechanism in the deposition reaction represented by the foregoing equation (5), so that the condition of the electrolytic copper plating solution 13 can be identified accurately and quantitatively.

When using the thus obtained parameters, the condition of an electrolytic copper plating solution 13 used in a plating apparatus (not shown) is controlled and maintained, thereby enabling the physical properties and deposition properties of the copper plated film to be stably held.

Third Embodiment

An electrolytic copper plating solution analyzer according to a third embodiment of the invention is described.

As shown in FIG. 1, an electrolytic copper plating solution analyzer 110 of the present embodiment has an analysis unit 131 in place of the analysis unit 31 of the electrolytic copper plating solution analyzer 10 of the first embodiment.

The analysis unit 131 has an analysis unit body 142 instead of the analysis unit 42 of the analysis unit 31.

The description below is centered around a difference from the first embodiment.

A difference from the first embodiment resides in that the analysis unit body 142 makes use of the following equations (41) and (61) to (63) instead of the foregoing equations (1) to (4) so as to analyze the measured data of potential η.

It will be noted that the equations (61), (62) and (63) are the same as the equations (2), (3) and (4) in the first embodiment, respectively. Of the constants and variables used in the respective equations, those common to the first embodiment are not illustrated again.

[Math. 25]

$$\eta = A \cdot T \left[ \ln \left\{ \frac{i_i}{I} \exp\left(-B \cdot I \frac{C_a^*}{T_i} t\right) + \frac{i_a}{I} \left\{ 1 - \exp\left(-B \cdot I \frac{C_a^*}{T_i} t\right) \right\} \right\} \right] \quad (41)$$

$$A = \frac{R}{\alpha F} \quad (61)$$

$$B = \frac{I}{nFd} \quad (62)$$

$$C_a^* = \frac{kC_a}{BI} \quad (63)$$

The above equation (41) is an equation indicating a timewise change of the potential η in the case that a reaction mechanism different from the first embodiment is assumed as a reaction mechanism of the deposition reaction in the electrolytic copper plating solution 13.

With regard to the equation (41), the reaction mechanism of the deposition reaction of a copper plated film, which we found, is described.

When an electric current is applied to the electrolytic copper plating solution 13, a copper plated film starts to be deposited on a negative electrode (cathode electrode) by electrolysis, immediately after which an inhibitor and a promoter used as additives are adsorbed on the negative electrode to cover the surface of the copper plated film.

The copper plated film is deposited between the additive thin film layer adsorbed on the negative electrode surface and the surface of the negative electrode and is incorporated as a metal film. It will be noted that immediately after the start of deposition of the copper plated film, the degree of adsorption effect of the additives decreases in the order of inhibitor and promoter.

The equation (41) represents a simplified mechanism wherein the effect of leveler is omitted.

The reduction reaction of the Cu (II) ion to metallic copper (i.e. zero valent Cu) goes through the formation of a Cu(I) ion serving as an intermediate. Although most of the Cu(I) is reduced to metallic copper, part thereof binds with a chloride or a promoter component to form a Cu(I) species as side products and is stabilized, part of which remains on the surface of the deposited metallic copper.

Accordingly, as the deposition reaction of the copper plated film proceeds, the surface concentration of the Cu(I) species on the surface of the copper plated film increases. This Cu(I) species corresponds, for example, to a Cu(I) complex formed from the Cu(I) ion generated by the reaction between the promoter component in the electrolytic copper plating solution 13 and the electrode, and the complex has the catalytic action on the electrode reaction, for which a promotion effect appears.

Further, as the deposition reaction of the copper plated film proceeds, the Cu(I) species (e.g. Cu(I) complex) in the vicinity of the surface of the negative electrode increases in concentration. Immediately after the commencement of deposition of the copper plated film, the Cu(I) species is substituted for the inhibitor adsorbed on the negative electrode.

In the deposition of the copper plated film, an inhibitor component, and a promoter component, not forming a complex with the Cu(I) ion, are supplied on the surface of the negative electrode from the electrolytic copper plating solution 13 along with the Cu (II) ion. On the other hand, the inhibitor component and the promoter component existing on the surface of the negative electrode are desorbed. The balance of the additive components on the electrode surface moves to equilibrium due to these formation, adsorption and desorption.

According to the reference 2, in the reaction mechanism that the Cu(I) species complex on the surface of the negative electrode shows a promotion effect, the Cu(I) species include, aside from the Cu(I) species formed on and attached to the negative electrode surface as described above, the Cu(I) species formed on the negative electrode surface and then desorbed from the negative electrode, and the Cu(I) species formed in the electrolytic copper plating solution 13 (e.g. on the surface of an anode electrode in the electrolytic copper plating solution 13).

Such Cu(I) species, not present on the negative electrode surface, are considered to show a promotion effect (promotion function) different from the Cu(I) species on the surface of the negative electrode. When the Cu(I) species, not present on the negative electrode surface, moves to the surface of the negative electrode by diffusion, it takes part in the copper deposition reaction at the negative electrode and shows a promotion effect.

When the deposition reaction mechanism described above is applied to the reaction in the analysis container 12 of the electrolytic copper plating analyzer 110, such a reaction mechanism proceeds as follows: the Cu(I) species generated on the surface 37a of the working electrode 18 serving as a negative electrode is substituted for the inhibitor on the surface 37a in the course of the copper deposition reaction at the time of the measurement of the potential η as the deposition reaction proceeds; and the resulting Cu(I) species forms a complex at least with a promoter to show a promotion effect.

It will be noted that the promoter does not show any promotion effect by itself, but acts to stabilize the chemically instable Cu(I) species by formation of a complex with the Cu(I) species. The chemically instable Cu(I) species shows a promotion effect by formation of a complex at least with the promoter. For example, the chemically instable Cu(I) species shows a promotion effect by formation of complexes with a promoter, the decomposed matter of the promoter and a chloride.

How to obtain the above equations (41) and (61) to (63) is illustrated with respect to the difference from the equations (1) to (4) in the first embodiment.

As stated in the first embodiment, the equations (9) and (10) are established with respect to the current density $I_i$ of a region of the surface 37a occupied with the inhibitor and the current density $I_a$ of a region of the surface 37a occupied with the promoter.

The current density I on the surface 37a is the sum of the current densities $I_i$ and $I_a$ and thus, can be expressed by the following equation (51).

[Math. 26]

$$I = i_i \theta_i \exp\left[-\frac{\alpha_i F}{RT}\eta\right] + i_a \theta_a \exp\left[-\frac{\alpha_a F}{RT}\eta\right] \tag{51}$$

The values of the transfer coefficients $\alpha_i$, $\alpha_a$ are substantially equal to each other. Such a copper plating reaction is a reversible reaction, for which both of the transfer coefficients $\alpha_i$, $\alpha_a$ are considered to be approximately 0.5. Accordingly, the transfer coefficients $\alpha_i$, $\alpha_a$ can be replaced with a.

When using the transfer coefficient α, the following equations (52) and (53) are obtained from the above equation (51).

[Math. 27]

$$I = (i_i \theta_i + i_a \theta_a)\exp\left[-\frac{\alpha F}{RT}\eta\right] \tag{52}$$

$$\eta = \frac{RT}{\alpha F}\left[\ln\frac{i_i \theta_i + i_a \theta_a}{I}\right] \tag{53}$$

With respect to the variations of the coverages $\theta_i$, $\theta_a$, it is assumed that the initiator is adsorbed on the surface 37a at the initial stage of deposition of the copper plated film on the surface 37a based on such a reaction mechanism of the embodiments as described above, and the adsorbed inhibitor is substituted with the promoter with time.

According to the model of the reference, the coverage $\theta_i$ can be expressed by the equation (15) based on the diffusion equation.

The total of the coverages $\theta_i$, $\theta_a$ is "1" and thus, the coverage $\theta_a$ can be expressed by the following equation (55).

[Math. 28]

$$\theta_a = 1 - \exp\left[-\frac{1}{T_i}kC_a t\right] \tag{55}$$

The equations (15) and (55) are substituted into the equation (53) to obtain the following equation (56).

[Math. 29]

$$\eta = \frac{RT}{\alpha F}\left[\ln\left[\frac{i_i}{I}\exp\left(-\frac{1}{T_i}kC_a t\right) + \frac{i_a}{I}\left\{1 - \exp\left(-\frac{1}{T_i}kC_a t\right)\right\}\right]\right] \tag{56}$$

The above equation (56) is a relational equation representing a timewise change of the potential η derived on the basis of the model that where an inhibitor and a promoter are contained, the inhibitor adsorbed on the surface 37a is substituted with the promoter with time depending on the difference in adsorption rate between the respective components.

However, it has been found that a great difference occurs between the potential obtained by actual measurement and the potential η calculated by the equation (56).

As a result of extensive studies, it has been found that it might be better to assume other reaction mechanism than to consider that the promoter is brought from the electrolytic copper plating solution 13 by diffusion.

For example, the results of the measurement could be better illustrated when such a reaction mechanism is assumed that the Cu(I) species generated on the surface 37 of the working electrode 18 in the course of the deposition reaction of a copper plated film is substituted for the inhibitor on the surface 37a of the working electrode 18 as the deposition reaction of the copper plated film proceeds, and the Cu(I) species itself shows a promotion effect (promotion function).

Accordingly, in the above equation (41), the reaction rate k of the equation (56) is replaced by a factor including the current density I as shown in equation (20) like the first embodiment.

Next, the operation of the electrolytic copper plating solution analyzer 110 of the present embodiment is described centered around a method for analyzing an electrolytic copper plating solution according to the embodiment.

In order to identify the condition of an electrolytic copper plating solution 13 used in an appropriate plating apparatus (not shown) by means of the electrolytic copper plating solution analyzer 110, a preparation step, a potential measurement step and an analysis step of the method for analyzing an electrolytic copper plating solution according to this embodiment are carried out in this order.

The preparation step and the potential measurement step of the embodiment are the same as the preparation step and the potential measurement step of the first embodiment except that the electrolytic copper plating solution analyzer 110 is used in place of the electrolytic copper plating solution analyzer 10.

Next, the analysis step of the embodiment is carried out. The difference from the first embodiment resides in that this step is carried out by using the analysis unit 131 in place of the analysis unit 31 of the first embodiment.

This step is automatically started with the analysis unit 131 when a measurement time $t_m$ passes and all data measured with the potential measurement unit 28 during the measurement time $t_m$ are transmitted to the analysis unit 131.

In this embodiment, an analysis program calculating the parameters in the equation (41) is memorized in the analysis unit body 142. The analysis program enables the measured data of the potential η transmitted from the potential measurement unit 28 to be applied to the equation (41) to calculate parameters.

With the electrolytic copper plating solution analyzer, the effects of the respective components (promoter and inhibitor) of the plating solution are quantified in terms of parameters ($i_i$, $i_a$, $C_a^*/T_i$), enabling the condition of the plating solution to be identified.

The analysis method using the analysis program is not specifically limited. Analysis methods can be adopted including, for example, a curve fitting using a least-squares technique, an inclination of measured potentials, and an average value of measured potentials.

The constants used in the analysis including, for example, constants necessary for calculating the equations (61), (62), are memorized in the analysis unit body 142 beforehand.

When the analysis unit body 142 executes the analysis program, $p_{21}$, $p_{22}$ and $p_{23}$ (which may be sometimes abbreviated as parameters $p_{21}$ to $p_{23}$) represented by the following equations (37) to (39), respectively, are calculated as parameters.

In this embodiment, since the least-squares technique is used, the analysis unit body 142 works in such a way that appropriate initial values are set as the parameters $p_{21}$ to $p_{23}$, under which when the analysis program is executed, calculation is repeated while changing the parameters until a deviation from the measured data is converged to minimum in the least-squares technique. In this embodiment, the sum of squared residuals S is also calculated.

[Math. 30]

$$p_{21} = i_i \quad (37)$$

$$p_{22} = i_a \quad (38)$$

$$p_{22} = \frac{C_a^*}{T_i} \quad (39)$$

The calculated parameters $p_{21}$ to $p_{23}$, the function η(t), which is determined by the curve fitting, and the sum of squared residuals S are displayed on the display 43 along with a graph of the measured data.

These parameters $p_{21}$ to $p_{23}$ are ones, from which the condition of the electrolytic copper plating solution 13, i.e. the states of the inhibitor and the Cu(I) species, is known.

Hence, the combinations of the parameters $p_{21}$ to $p_{23}$ are a group of values identifying the condition of the electrolytic copper plating solution 13.

The parameters $p_{21}$ and $p_{22}$, respectively, correspond to exchange current densities $i_i$ and $i_a$. When the effects of the inhibitor and Cu(I) species increase, respectively, the magnitudes of the exchange current densities $i_i$ and $i_a$ change.

The parameter $p_{23}$ corresponds to $C_a^*/T_i$ and is thus a parameter indicating a ratio between the promotion effect and the inhibition effect.

It will be seen that if the parameter $p_{23}$ increases, the promotion effect increases relatively to the inhibition effect. It will also be seen that when the parameter $p_{23}$ decreases, the inhibition effect increases relatively to the promotion effect.

When the parameters $p_{21}$ to $p_{23}$ extend beyond a certain range, respectively, the balance of the respective effects is disrupted, thus leading to the occurrence of a failure.

For example, such an phenomenon appears that with via-filling plating, the degree of filling of plated copper in the via hole lowers.

Whether or not the condition of the electrolytic copper plating solution 13 identified with these parameters $p_{21}$ to $p_{23}$ is good can be judged if the judgment conditions are preset.

Such a judgment may be made by a measurer after viewing the results of the respective parameters displayed on the display 43. Alternatively, the analysis unit body 142, in which the judgment conditions have been memorized, may automatically judge the condition by comparison between the values of the parameters and the judgment conditions. If the analysis unit body 142 judges the condition, the results of the judgment are displayed on the display 43 along with the values of the respective parameters.

In this way, the analysis step is completed.

According to the electrolytic copper plating solution analyzer 110 of the present embodiment, the potential η between the working electrode 18 and the reference electrode 19, both immersed in an analysis sample of the electrolytic copper plating solution 13, is measured, and the relation between an elapsed time t and the potential η is analyzed to calculate parameters indicating the condition of the electrolytic copper plating solution 13.

According to the analysis, the parameters indicating the condition of the electrolytic copper plating solution 13 can be obtained based on such a reaction mechanism that the Cu(I) species generated on the surface 37a of the working electrode 18 during the deposition reaction of a copper plated film is substituted for the inhibitor located on the surface 37a as the deposition reaction of the copper plated film proceeds, and the Cu(I) species shows a promotion function by formation of a complex at least with a promoter.

The parameters identified in this way are calculated on basis of the model of a reaction mechanism in the deposition reaction expressed by the equation (41) and thus, can identify the condition of the electrolytic copper plating solution 13 accurately and quantitatively.

When using the thus obtained parameters, the condition of the electrolytic copper plating solution 13 used in a plating solution (not shown) can be controlled and maintained, enabling the physical properties and deposition properties to be stably held.

Fourth Embodiment

An electrolytic copper plating solution analyzer of a fourth embodiment of the invention is described.

As shown in FIG. 1, an electrolytic copper plating solution analyzer 160 of the present embodiment has an analysis unit 181 in place of the analysis unit 31 of the electrolytic copper plating solution analyzer 10 of the first embodiment The analysis unit 181 has an analysis unit body 192 instead of the analysis unit 42 of the analysis unit 31.

The description below is centered around a difference from the first embodiment

The difference from the first embodiment resides in that the analysis unit body 192 analyzes the measured data of potential η by using the following equations (42) and (64) to (66) in place of the foregoing equations (1) to (4).

It will be noted that the equations (64), (65) and (66) are the same as the equations (2), (3) and (4) in the first embodiment, respectively. Among the constants and variables used in the respective equations, illustration of those common to the first embodiment are omitted.

[Math. 31]

$$\eta = A \cdot T\left[\ln\left(\frac{i_a}{I}\right) + \ln\left\{1 - \exp\left(-B \cdot I \frac{C_a^*}{T_i}t\right)\right\}\right] \quad (42)$$

$$A = \frac{R}{\alpha F} \quad (64)$$

$$B = \frac{I}{nFd} \quad (65)$$

$$C_a^* = \frac{kC_a}{BI} \quad (66)$$

The above equation (42) is one that indicates a timewise change of the potential η in the case where a reaction mechanism different from the case of the first embodiment is assumed as a reaction mechanism of deposition reaction in the electrolytic copper plating solution 13.

The equation (42) is an equation indicating a timewise change of the potential η in the case where a reaction mechanism same as that of the third embodiment is assumed as a reaction mechanism of deposition reaction in the electrolytic copper plating solution 13. For simplification of calculation, this equation indicates such a state that an elapsed time t becomes large sufficient that the surface 37a of the working electrode 18 covered with an inhibitor is in the state of being well substituted with a promoter.

If the elapsed time t of the equation (53) is small, the exchange current density $i_a$ of the region occupied by the promoter is considered to be greater than the exchange current density $i_i$ of the region occupied by the inhibitor. However, in the state that the elapsed time t becomes adequately large and the surface 37a of the working electrode 18 covered with the inhibitor is well replaced with the promoter, the value of (exchange current density $i_i$×coverage $\theta_i$) becomes much smaller than the value of (exchange current density $i_a$×coverage $\theta_a$).

Accordingly, the equation (53) can be deformed to the equation (58) indicated below.

[Math. 32]

$$\eta = \frac{RT}{\alpha F}\left[\ln\frac{i_a \theta_a}{I}\right] \quad (58)$$

When the equation (55) is substituted into the equation (58), there can be obtained the following equation (59) indicating the relation between the elapsed time t and the potential η.

[Math. 33]

$$\eta = \frac{RT}{\alpha F}\left[\ln\left(\frac{i_a}{I}\right) + \ln\left\{1 - \exp\left(-\frac{kC_a}{T_i}t\right)\right\}\right] \quad (59)$$

Since the reaction mechanism assumed in the fourth embodiment is same as that of the third embodiment, the results of the measurement could be better illustrated, in the above equation (59) as with the case of the foregoing equation (56) of the third embodiment, based on the assumption, for example, of such a reaction mechanism that the Cu(I) species generated on the surface 37a of the working electrode 18 in the course of the deposition reaction of a copper plated film is substituted for the inhibitor on the surface 37a of the working electrode 18 as the deposition reaction of the copper plated film proceeds, so that the Cu(I) species itself shows a promotion function.

Accordingly, the reaction rate k in the equation (59) is replaced, in the equation (42), by a factor including the current density I as indicated in the equation (20) like the first embodiment.

Next, the operation of the electrolytic copper plating solution analyzer 160 of the present embodiment is described centered around a method for analyzing an electrolytic copper plating solution according to this embodiment.

In order to identify the condition of the electrolytic copper plating solution 13 used in an appropriate plating apparatus (not shown) by means of the electrolytic copper plating solution analyzer 160, a preparation step, a potential measurement step and an analysis step of the method for analyzing an electrolytic copper plating solution according to the present embodiment are carried out in the order.

The preparation and potential measurement steps of the embodiment are similar to the preparation and potential measurement steps of the first embodiment except that the electrolytic copper plating solution analyzer 160 is used in place of the electrolytic copper plating solution analyzer 10.

Next, the analysis step of the embodiment is performed. A difference from the first embodiment resides in that this step is carried out using an analysis unit 181 instead of the analysis unit 31 of the first embodiment.

This step is automatically started with the analysis unit 181 when a measurement time $t_m$ elapses and all measurement data measured with the potential measurement unit 28 during the measurement time $t_m$ are transmitted to the analysis unit 181.

In the present embodiment, an analysis program calculating the parameters of the equation (42) is memorized in an analysis unit body 192. The analysis program serves to apply the measured data of potential η transmitted from the potential measurement unit 28 to the equation (42) to calculate parameters.

With the electrolytic copper plating solution analyzer, the effects of the respective components (promoter and inhibitor) in the plating solution are quantified in terms of parameters ($i_a$ and $C_a^*/T_i$), thus enabling the condition of the plating solution to be identified.

The analysis method using the analysis program is not specifically limited. For example, there can be adopted analysis methods such as of a curve fitting using a least-squares technique, an inclination of measured potentials, an average value of measured potentials and the like.

The constant used for the analysis, e.g. constants necessary for the calculation of the equations (64), (65), have been memorized in the analysis unit body 192 beforehand.

When the analysis program is executed by the analysis unit body 192, $p_{31}$ and $p_{32}$ (which may be sometimes abbreviated as parameters $p_{31}$, $p_{32}$) represented by the following equations (67), (68) are calculated as parameters.

In the present embodiment, since the least-squares technique is used, the analysis unit body 192 works in such a way that appropriate initial values are set as the parameters $p_{31}$, $p_{32}$, under which when the analysis program is executed, calculation is repeated while changing the parameters until a deviation from the measured data is converged to minimum in the least-squares technique. In this embodiment, the sum of squared residuals S is also calculated.

[Math. 34]

$$p_{31} = i_a \qquad (67)$$

$$p_{32} = \frac{C_a^*}{T_i} \qquad (68)$$

The thus calculated parameters $p_{31}$, $p_{32}$, the function $\eta(t)$ determined by the curve fitting, and the sum of squared residuals S are displayed on the display 43 along with the graph of the measured data.

These parameters $p_{31}$, $p_{32}$ are ones, from which the condition of the electrolytic copper plating solution 13, i.e. the states of the inhibitor, Cu(I) species and leveler, can be known.

Accordingly, the combination of the parameters $p_{31}$, $p_{32}$ is a group of values capable of identifying the condition of the electrolytic copper plating solution 13.

The parameter $p_{31}$ corresponds to an exchange current density $i_a$. If the effect of the Cu(I) species increases, the magnitude of the exchange density $i_a$ changes.

The parameter $p_{32}$ corresponds to $C_a^*/T_i$ and is a parameter indicating a ratio between the promotion effect and the inhibition effect.

It will be seen that an increase of the parameter $p_{32}$ leads to a relative increase of the promotion effect compared to the inhibition effect.

If the parameters $p_{31}$ and $p_{32}$ go beyond certain ranges, respectively, the balance between the respective effects is disrupted, thus leading the occurrence of a failure.

For instance, such a phenomenon appears that with via-filling plating, the degree of filling of plated copper in the via hole lowers.

Whether or not the condition of the electrolytic copper plating solution 13 identified with these parameters $p_{31}$, $p_{32}$ is good can be judged by setting judgment conditions beforehand as in the first embodiment. Such a judgment may be made by a measurer while checking the respective parameters displayed on the display 43. Alternatively, the judgment conditions may be memorized in the analysis unit body 192, followed by automatic judgment with the analysis unit body 192 by comparison between the values of the respective parameters and the judgment conditions. In the case where the judgment is made with the analysis unit body 192, the results of the judgment are displayed on the display 43 along with the values of the respective parameters.

In this way, the analysis step is completed.

According to the electrolytic copper plating solution analyzer 160 of the present embodiment, the potential $\eta$ between the working electrode 18 and the reference electrode 19, both immersed in an analysis sample of the electrolytic copper plating solution 13, is measured, and the relation between an elapsed time t and the potential $\eta$ is analyzed, thereby enabling parameters indicating the condition of the electrolytic copper plating solution 13 to be calculated.

In the course of the analysis, the parameters indicating the condition of the electrolytic copper plating solution 13 can be obtained based on such a reaction mechanism: the Cu(I) species generated on the surface 37a of the working electrode 18 in the course of the deposition reaction of a copper plated film is substituted for an inhibitor located on the surface 37a as the deposition reaction of the copper plated film proceeds; and a leveler is substituted for the inhibitor located on the surface 37a as the deposition reaction of the copper plated film proceeds, with the results that the Cu(I) species shows a promotion effect by formation of a complex at least with a promoter.

The parameters specified in this way are calculated based on the model of the reaction mechanism in the deposition reaction represented by the foregoing equation (42), so that the condition of the electrolytic copper plating solution 13 can be identified accurately and quantitatively.

When the condition of the electrolytic copper plating solution 13 used in a plating apparatus (not shown) is controlled and maintained by use of the thus obtained parameters, the physical properties and deposition properties of the copper plated film can be stably held.

In the foregoing, the preferred embodiments of the invention including the first, second, third and fourth embodiments have been described in detail. The invention should not be construed as limited to these embodiments, and many changes and alterations may be possible within the scope of the invention set forth in the claims.

For example, illustration has been made in the foregoing embodiments with respect to the case that the electrolytic copper plating solution analyzers are those separated from a plating apparatus (not shown). However, a plating vessel (not shown) of a plating apparatus may be connected, for example, to the analysis container 12 shown in FIG. 1 through a line (not shown) so as to feed an electrolytic copper plating solution in the vessel to the analysis container 12 via the line.

On the assumption of the reaction mechanisms in the analysis step in the illustration of the foregoing embodiments, objects to be substituted with a leveler differ from each other. More particularly, the reaction mechanism in the first embodiment is assumed such that as the deposition reaction of a copper plated film proceeds in the electrolytic copper plating solution 13, a leveler in the electrolytic copper plating solution is substituted for the Cu(I) species located on the surface 37a of the working electrode 18. In contrast, with the second embodiment, such a reaction mechanism is assumed that a leveler is substituted for an inhibitor located on the surface 37a.

Although it is supposed that with a leveler used in an electrolytic copper plating solution, either of the substitutions occurs and that the ratio of the respective substitution occurrences differs depending on the type of leveler and the types of the components in the electrolytic copper plating solution 13.

Accordingly, in order to identify the condition of the electrolytic copper plating solution 13 in higher accuracy, it is preferred to choose, from the equations (1) and (5), a relational equation wherein a fitting error between the fitting curve and the measured data is made smaller upon calculation of parameters.

In the third and fourth embodiments, the effect of the leveler is omitted.

With the equations (41) and (42) wherein the effect of the leveler is excluded, although the processing rates of the analysis unit bodies 142, 192 become high, the fitting error between the fitting curve and the measured data becomes slightly large.

For instance, it is preferred that the analysis programs based on the equations (1), (5), (41) and (42) are built in the analysis unit so as to enable the selection of any of the equations.

On this occasion, the selection judgment standards to be adopted may be ones based on the selection of a program giving a smaller value with respect to the sum of residual squares. Alternatively, the analysis processing speed may be prioritized.

In the case where the type of electrolytic copper plating solution 13 to be analyzed is determined, an evaluation test has been preliminarily performed and an analysis program more suited for the electrolytic copper plating solution 13 can be stored.

In the illustration of the foregoing embodiments, although the electrolytic copper plating solution analyzers and the methods for analyzing an electrolytic copper plating solution have been described, the present invention should not be construed as limited to the analysis of electrolytic copper plating. For example, when using a constant current electrolysis, the invention can be applied to the analysis of electrolytic plating solutions other than additives including a promoter, an inhibitor and a leveler and also copper plating solutions containing additives including a promoter and an inhibitor. For instance, the invention is also applicable to an electrolytic nickel plating solution analyzer and a method of analyzing an electrolytic nickel plating solution. In this regard, however, with the case of the electrolytic nickel plating that differs in reaction mechanism from electrolytic copper plating, parameters identifying the condition of the electrolytic nickel plating solution are calculated based on the reaction mechanism that an added promoter shows a promotion function. In this case, as to the coefficients of the foregoing equations (1) to (8) and (61) to (66) the term "at the time of the deposition reaction of a copper plated film" should read as "at the time of the deposition reaction of a nickel plated film".

EXAMPLES

The examples of the respective embodiments are now described, which should not be construed as limiting the invention thereto.

Examples 1 to 8 deal mainly with the comparison of curve-fitting properties.

In Examples 9 to 28, condition identifications of plating solutions are compared with one another.

Figure 3:
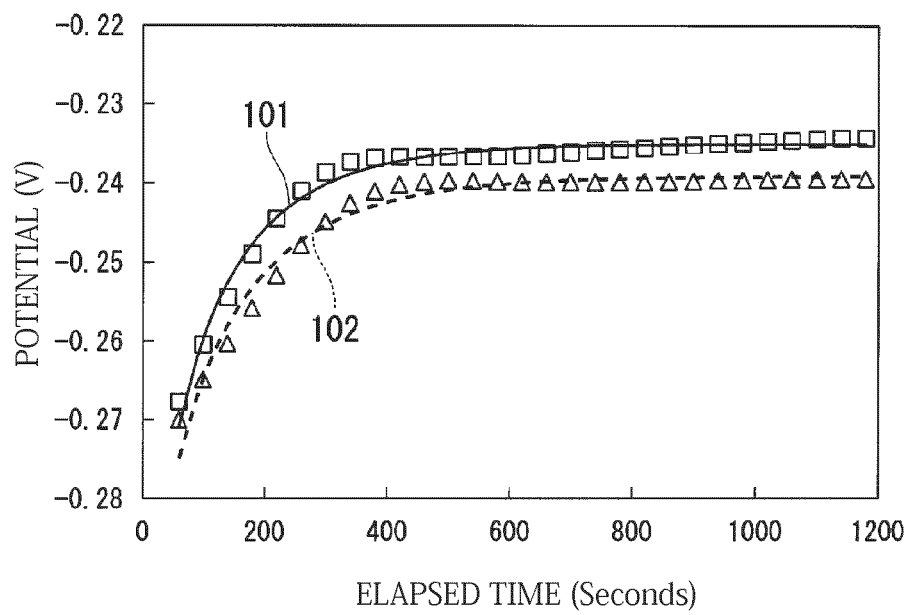
FIG. 3 is a graph showing an example of data of measurement and results of analysis in Examples 1 and 2 making use of an electrolytic copper plating apparatus according to a first embodiment of the invention.
Figure 4:
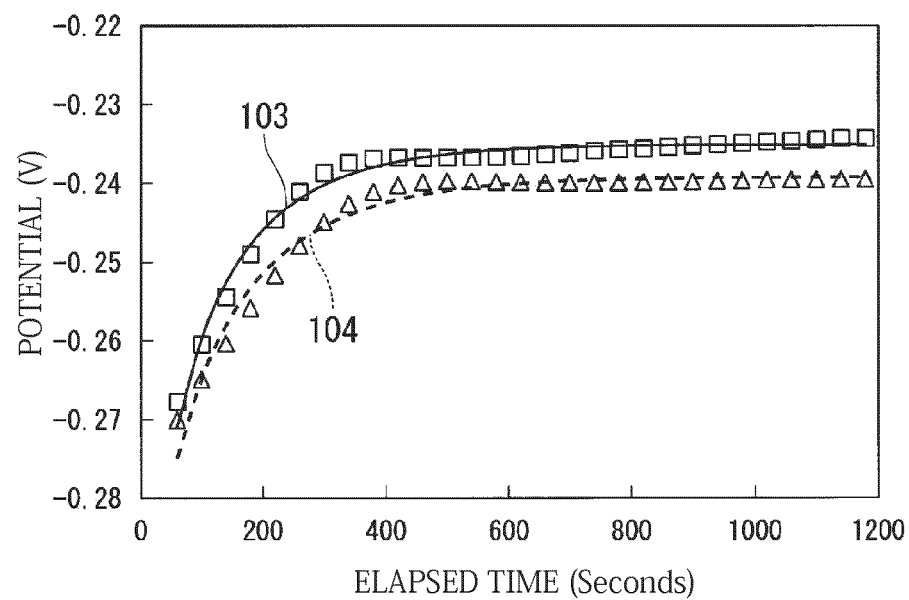
FIG. 4 is a graph showing an example of data of measurement and results of analysis in Examples 3 and 4 making use of an electrolytic copper plating apparatus according to a second embodiment of the invention.
Figure 5:
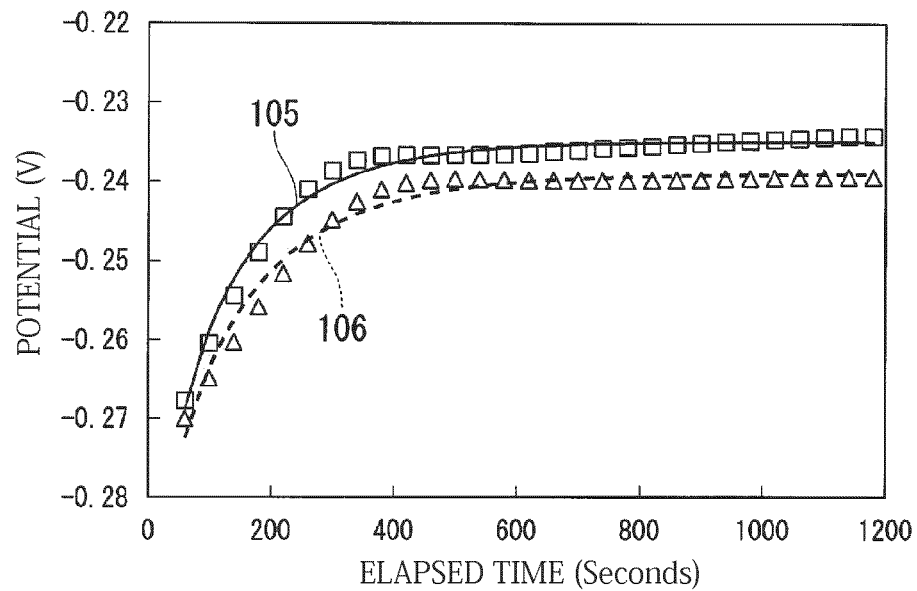
FIG. 5 is a graph showing an example of data of measurement and results of analysis in Examples 5 and 6 making use of an electrolytic copper plating apparatus according to a third embodiment of the invention.
Figure 6:
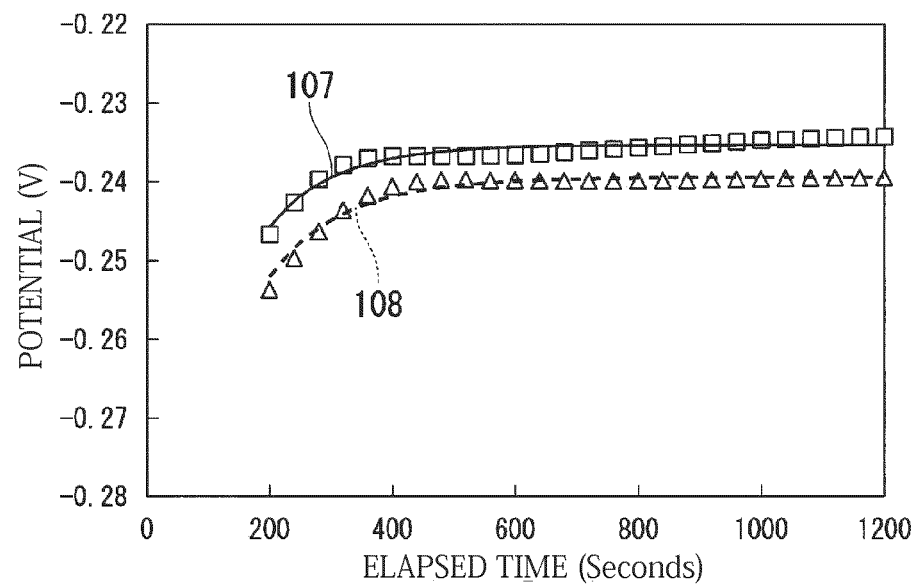
FIG. 6 is a graph showing an example of data of measurement and results of analysis in Examples 7 and 8 making use of an electrolytic copper plating apparatus according to a fourth embodiment of the invention.

FIG. 3 is a graph showing an example of measurement data and the results of analysis in Examples 1 and 2 using the electrolytic copper plating solution analyzer of the first embodiment of the invention. FIG. 4 is a graph showing another example of measurement data and the results of analysis in Examples 3, 4 using the electrolytic copper plating solution analyzer of the second embodiment of the invention. FIG. 5 is a graph showing a further example of measurement data and the results of analysis in Examples 5 and 6 using the electrolytic copper plating solution analyzer of the third embodiment of the invention. FIG. 6 is a graph showing a still further example of measurement data and the results of analysis in Examples 7 and 8 using the electrolytic copper plating solution analyzer of the fourth embodiment of the invention.

In the respective graphs, the abscissa indicates an elapsed time t (seconds) and the ordinate indicates a potential $\eta$ (V). It will be noted that the potential $\eta$ is a value converted in terms of the redox potential reference of copper.

In Examples 1 to 28, electrolytic copper plating solutions 13 being used in a plurality of plating apparatus (not shown) were used and analyzed according to the following method, respectively.

<Measurement Samples>

As measurement samples, measurement samples $P_1$, $P_2$ were collected from an electrolytic copper plating solution 13 being used in a first plating solution (not shown). The measurement samples $P_1$, $P_2$ were, respectively, electrolytic copper plating solutions 13 collected in different times. Accordingly, the conditions of additives of the measurement samples $P_1$, $P_2$ were not the same.

Measurement samples $P_3$ to $P_7$ were collected from an electrolytic copper plating solution 13 being used in a second plating apparatus (not shown) different from the first plating apparatus. The formations of the plating solutions of the first and second plating apparatus were different from each other.

Among the measurement samples $P_3$ to $P_7$, $P_3$ and $P_4$ were samples whose condition of the plating solution was bad, and $P_5$ to $P_7$ were samples having a good condition.

The difference between the good and bad conditions of the plating solutions was judged according to whether the embedding or hole-filling properties were good or bad when bottom-up deposition was carried out for via holes. More particularly, the section of the via hole after plating was observed, and the case that the via hole was filled to not less than 50% of its capacity was judged as "good" and the case that the via hole was filled only to less than 50% was judged as "bad".

In the respective measurements, the fractions of the electrolytic copper plating solutions 13 were taken from the measurement samples $P_1$ to $P_7$ and used for the measurement.

Subsamples 1-1, 1-2, 1-3 and 1-4 were taken from the measurement sample $P_1$. These subsamples 1-1, 1-2, 1-3 and 1-4 were the same with respect to the condition as an electrolytic copper plating solution.

Likewise, subsamples n-1, n-2, n-3 and n-4 were taken from the measurement sample $P_n$ (wherein n=2 to 7). Hence, the subsamples n-1, n-2, n-3 and n-4 were the same with respect to the condition as an electrolytic copper plating solution.

Examples 1 and 2

In Examples 1 and 2, the respective subsamples 1-1 and 2-1 were, analyzed by use of an electrolytic copper plating solution analyzer 10.

A platinum disk electrode was used as a working electrode 18. The area of a surface 37a was set at $4\pi$ mm$^2$.

An electrode made of silver/silver chloride (Ag/AgCl) was used as a reference electrode 19. A counter electrode 21 used was a circular cylindrical electrode having a diameter of 8 mm and made of copper.

The measurement conditions of potential η in a potential measurement unit 28 were such that a current density I in the working electrode was 1 A/dm$^2$, the rotation rate of the working electrode 18 was 2500 rpm, and the temperature of the subsamples 1-1, 2-1 for the measurement of the potential was set at 30° C. (303.15 K).

The measurement data of Examples 1, 2 are indicated by symbol □ (subsample 1-1) and symbol Δ (subsample 2-1) in the graph of FIG. 3. It will be noted that in FIG. 3, although the measurement data are shown as thinned out for easy-to-see convenience, they are measured at intervals of one second.

Among these measurement data, potential data within a range of 50 seconds to 1200 seconds in elapsed time t were used to analyze the condition of the subsamples 1-1 and 2-1 with an analysis unit 31.

The fitting curves applied by use of the equation (1) are shown in FIG. 3 as curves 101 and 102. The curve 101 (solid line) is a fitting curve of the measurement data of the subsample 1-1, and the curve 102 (broken line) is a fitting curve of the measurement data of the subsample 2-1.

In the electrolytic copper plating solution analyzer 10, the graphs shown in FIG. 3 are sequentially displayed on the display 43.

The parameters $p_1$ to $p_5$ calculated by the analysis unit 31 are indicated in Table 1 below. In this regard, however, the units of the parameters $p_1$ to $p_3$ are all mA/cm$^2$, the unit of $p_4$ is 1/cm, and the unit of $p_5$ is 1/second (which are true in Examples 9 to 13). The constants used for the calculation are such that gas constant R is 8.314 J/(mol-K), transfer coefficient α is 0.5 eq/mol, Faraday constant F is 96480 C/eq, the molar density of copper d is 0.141 mols/cm$^3$, and the valence of copper n is 2 eq/mol (which are true in Examples 3 to 28).

TABLE 1

| Parameter | Unit | Example 1 | Example 2 | Remarks |
|---|---|---|---|---|
| $p_1$ | mA/cm$^2$ | 0.0275 | 0.0289 | $i_l$ |
| $p_2$ | mA/cm$^2$ | 0.111 | 0.103 | $i_a$ |
| $p_3$ | mA/cm$^2$ | 1.265 | 1.281 | $i_l$ |
| $p_4$ | 1/cm | 19.0 | 16.8 | $C_a^*/T_i$ |
| $p_5$ | 1/second | 33.5 | 30.5 | $k_2C_l/T_i$ |

Examples 3 and 4

In Examples 3 and 4, the subsamples 1-2 and 2-2 were, respectively, analyzed by use of an electrolytic copper plating solution analyzer 60. The conditions of the working electrode 18, reference electrode 19 and counter electrode 21 and the measurement conditions of the potential were the same as those of Example 1.

In FIG. 4, the measurement data of Examples 3, 4 are indicated by symbol □ (subsample 1-2) and also by symbol Δ (subsample 2-2). It will be noted that in FIG. 4, although the measurement data are shown as thinned out for easy-to-see convenience, they are measured at intervals of one second.

Among these measurement data, potential data within a range of 50 seconds to 1200 seconds in elapsed time t were used to analyze the condition of the subsamples 1-2 and 2-2 with an analysis unit 81.

The fitting curves applied by use of the equation (5) are shown in FIG. 4 as curves 103 and 104. The curve 103 (solid line) is a fitting curve of the measurement data of the subsample 1-2, and the curve 104 (broken line) is a fitting curve of the measurement data of the subsample 2-2.

In the electrolytic copper plating solution analyzer 60, the graphs shown in FIG. 4 are sequentially displayed on the display 43.

The parameters $p_{11}$ to $p_{15}$ calculated by the analysis unit 81 are indicated in Table 2 below.

In this regard, however, the units of the parameters $p_{11}$ to $p_{13}$ are all mA/cm$^2$, the unit of $p_{14}$ is 1/cm, and the unit of $p_{15}$ is 1/second (which are true in Examples 14 to 18).

TABLE 2

| Parameter | Unit | Example 3 | Example 4 | Remarks |
|---|---|---|---|---|
| $p_{11}$ | mA/cm$^2$ | 0.732 | 1.046 | $i_l$ |
| $p_{12}$ | mA/cm$^2$ | 0.111 | 0.102 | $i_a$ |
| $p_{13}$ | mA/cm$^2$ | 0.029 | 0.029 | $i_l$ |
| $p_{14}$ | 1/cm | 15.5 | 12.2 | $C_a^*/T_i$ |
| $p_{15}$ | 1/second | 0.0058 | 0.0046 | $k_3C_l/T_i$ |

Examples 5 and 6

In Examples 5 and 6, the subsamples 1-3 and 2-3 were, respectively, analyzed by use of the above electrolytic copper plating solution analyzer. The conditions of the working electrode 18, reference electrode 19 and counter electrode 21 and the measurement conditions of the potential were the same as those of Example 1.

In FIG. 5, the measurement data of Examples 5, 6 are indicated by symbol □ (subsample 1-3) and also by symbol Δ (subsample 2-3). It will be noted that in FIG. 5, although the measurement data are shown as thinned out for easy-to-see convenience, they are measured at intervals of one second.

Among these measurement data, potential data within a range of 50 seconds to 1200 seconds in elapsed time t were used to analyze the condition of the subsamples 1-3 and 2-3 with an analysis unit 131.

The fitting curves applied by use of the equation (41) are shown in FIG. 5 as curves 105 and 106. The curve 105 (solid line) is a fitting curve of the measurement data of the subsample 1-3, and the curve 106 (broken line) is a fitting curve of the measurement data of the subsample 2-3.

In the electrolytic copper plating solution analyzer 110, the graphs shown in FIG. 5 are sequentially displayed on the display 43.

Examples 7, 8

In Examples 7 and 8, the subsamples 1-4 and 2-4 were, respectively, analyzed by use of an electrolytic copper plating solution analyzer 160. The conditions of the working electrode 18, reference electrode 19 and counter electrode 21 and the measurement conditions of the potential were the same as those of Example 1.

In FIG. 6, the measurement data of Examples 7, 8 are indicated by symbol □ (subsample 1-4) and also by symbol Δ (subsample 2-4). It will be noted that in FIG. 6, although the measurement data are shown as thinned out for easy-to-see convenience, they are measured at intervals of one second.

Among these measurement data, potential data within a range of 200 seconds to 1200 seconds in elapsed time t were used to analyze the condition of the subsamples 1-4 and 2-4 with an analysis unit 181.

The fitting curves applied by use of the equation (42) are shown in FIG. 6 as curves 107 and 108. The curve 107 (solid line) is a fitting curve of the measurement data of the subsample 1-4, and the curve 108 (broken line) is a fitting curve of the measurement data of the subsample 2-4.

In the electrolytic copper plating solution analyzer 160, the graphs shown in FIG. 6 are sequentially displayed on the display 43.

For the comparison between the results of the analysis of Examples 1, 3, 5 and 7 (the curves 101, 103, 105 and 107 of FIGS. 3, 4, 5 and 6, respectively) and the results of the analysis of Examples 2, 4, 6, 8 (the curves 102, 104, 106 and 108 of FIGS. 3, 4, 5 and 6, respectively), which are, respectively, corresponded in the condition of the subsamples, the sum of residual squares S ($V^2$) in the respective analyses is indicated in Table 3 below.

TABLE 3

|  | Sum of residual squares S ($V^2$) |
|---|---|
| Example 1 | $3.1 \times 10^{-5}$ |
| Example 3 | $3.1 \times 10^{-5}$ |
| Example 5 | $3.4 \times 10^{-5}$ |
| Example 7 | $1.9 \times 10^{-5}$ |
| Example 2 | $4.1 \times 10^{-5}$ |
| Example 4 | $3.4 \times 10^{-5}$ |
| Example 6 | $4.5 \times 10^{-5}$ |
| Example 8 | $1.3 \times 10^{-5}$ |

<Discussion on the Results of Analysis of Examples 1 to 8>

As shown in Table 1, the parameters $p_2$, $p_4$ become larger in Example 1 than in Example 2.

This is assumed that the work of the Cu(I) species showing a promotion effect (promotion function) by formation of a complex at least with the promoter becomes excessive against the inhibitor in Example 1. According to the reference 2, if the Cu(I) species showing the promotion effect by formation at least with a promoter works excessively, the via-hole filling characteristics become worsened. From this, it will be seen that according to the analysis using the electrolytic copper plating solution analyzer 10, when using the electrolytic copper plating solution $P_1$, the via-hole filling characteristics become poor.

As shown in Table 2, the parameters $p_{12}$, $p_{14}$ become larger in Example 3 than in Example 4.

This is assumed that the work of the Cu(I) species showing a promotion effect (promotion function) by formation of a complex at least with the promoter becomes excessive against the inhibitor in Example 3. According to the reference 2, if the Cu(I) species showing the promotion effect by formation at least with a promoter works excessively, the via-hole filling characteristics become worsened. From this, it will be seen that according to the analysis using the electrolytic copper plating solution analyzer 60, when using the electrolytic copper plating solution $P_1$, the via-hole filling characteristics become poor.

As shown in Table 3, when the sums of residual squares S in Examples 1, 3, 5 and 7 using the subsamples 1-1, 1-2, 1-3 and 1-4, which are taken from the measurement sample $P_1$ having the same condition, are compared with one another, the sums of residual squares S of Examples 1, 3 are substantially equal to each other and the sum of residual squares S of Example 5 is larger by about 10% than the former. Since the measured time differs between Examples 1, 3, 5 and Example 7, a direction comparison of the sums of residual squares S cannot be made. Nevertheless, it can be confirmed that there is no great difference between the sum of residual squares S of Example 7 and the sums of residual squares S of Examples 1, 3 and 5.

It can be said that a smaller sum of residual squares S results in the better approximation of the fitting curve to the measurement data. Accordingly, it is possible to say that the calculated parameters better represent the condition of the electrolytic copper plating solution 13. In this sense, a smaller sum of residual squares S leads to more accurate control of additives.

Thus, it has been confirmed that the more accurate control of additives is enabled in the analyses with the electrolytic copper plating solution analyzers 10, 60 of Examples 1 and 3 wherein the effect of a leveler is taken into account than in the analysis with the electrolytic copper plating solution analyzer of Example 5 wherein no consideration is taken for the leveler effect.

When Examples 2, 4, 6, 8 using the subsamples 2-1, 2-2, 2-3, 2-4, which were taken from the measurement sample $P_2$ and having the same condition, are compared with one another with respect to the sum of residual squares S, it increases in the order of Examples 4, 2 and 6. Example 6 increases by about 22% and about 10% when compared with Examples 4, 2, respectively. With respect to Examples 2, 4, 6 and Example 8 which differ in measured time from each other, a direct comparison of the sums of residual squares S cannot be made. Nevertheless, it can be confirmed that there is no great difference between the sum of residual squares S of Example 8 and the sums of residual squares S of Examples 2, 4, 6.

Thus, it has been confirmed that the more accurate control of additives is enabled in the analyses with the electrolytic copper plating solution analyzers 10, 60 of Examples 2, 4 wherein the effect of a leveler is taken into account than in the analysis with the electrolytic copper plating solution analyzer of Example 6 wherein no consideration is taken for the leveler effect.

Examples 9 to 13

In Examples 9 to 13, subsamples 3-1, 4-1, 5-1, 6-1, 7-1 were analyzed by use of the electrolytic copper plating solution analyzer 10, respectively. The conditions of the working electrode 18, reference electrode 19 and counter electrode 21 and the measurement conditions of the potential were the same as in Example 1.

Among these measurement data, potential data within a range of 50 seconds to 1200 seconds in elapsed time t were used to analyze the condition of the subsamples 3-1, 4-1, 5-1, 6-1 and 7-1 with an analysis unit 31.

The parameters $p_1$ to $p_5$ calculated by the analysis unit 31 and the results of judgment of the condition of the plating solutions are shown in Tables 4, 5, respectively.

TABLE 4

| Parameter | Unit | Example 9 | Example 10 | Example 11 | Example 12 | Example 13 | Remarks |
|---|---|---|---|---|---|---|---|
| $p_1$ | mA/cm² | 0.358 | 1.049 | 2.499 | 3.611 | 2.719 | $i_i$ |
| $p_2$ | mA/cm² | 0.066 | 0.105 | 0.091 | 0.111 | 0.105 | $i_a$ |
| $p_3$ | mA/cm² | 0.048 | 0.025 | 0.084 | 0.136 | 0.121 | $i_l$ |
| $p_4$ | 1/cm | 3.6 | 12.4 | 37.1 | 52.7 | 48.9 | $C_a^*/T_i$ |
| $p_5$ | 1/second | 0.0019 | 0.0048 | 0.0130 | 0.0185 | 0.0170 | $k_2C_l/T_i$ |

TABLE 5

| Parameter | Unit | Individual judgment standards | Example 9 | Example 10 | Example 11 | Example 12 | Example 13 |
|---|---|---|---|---|---|---|---|
| $p_1$ | mA/cm² | 1.5-4.0 | outside the range | outside the range | within the range | within the range | within the range |
| $p_2$ | mA/cm² | 0.08-0.20 | outside the range | within the range | within the range | within the range | within the range |
| $p_3$ | mA/cm² | 0.07-0.15 | outside the range | outside the range | within the range | within the range | within the range |
| $p_4$ | 1/cm | 20.0-60.0 | outside the range | outside the range | within the range | within the range | within the range |
| $p_5$ | 1/second | 0.01-0.10 | outside the range | outside the range | within the range | within the range | within the range |
| | | Judgment result of analysis | bad | bad | good | good | good |
| | | Judgment result of measurement | bad | bad | good | good | good |

Examples 14 to 18

In Examples 14 to 18, the subsamples 3-2, 4-2, 5-2, 6-2 and 7-2 were, respectively, analyzed by use of an electrolytic copper plating solution analyzer 60. The conditions of the working electrode 18, reference electrode 19 and counter electrode 21 and the measurement conditions of the potential were the same as those of Example 1.

Among these measurement data, potential data within a range of 50 seconds to 1200 seconds in elapsed time t were used to analyze the condition of the subsamples 3-2, 4-2, 5-2, 6-2 and 7-2 by means of an analysis unit 81.

The parameters $p_{11}$ to $p_{15}$ calculated by the analysis unit 81 and the judgment results of the condition of the plating solutions are shown in Tables 6 and 7, respectively.

TABLE 6

| Parameter | Unit | Example 14 | Example 15 | Example 16 | Example 17 | Example 18 | Remarks |
|---|---|---|---|---|---|---|---|
| $p_{11}$ | mA/cm² | 0.398 | 0.393 | 0.347 | 0.336 | 0.361 | $i_i$ |
| $p_{12}$ | mA/cm² | 0.473 | 0.488 | 0.432 | 0.438 | 0.452 | $i_a$ |
| $p_{13}$ | mA/cm² | 0.123 | 0.116 | 0.106 | 0.117 | 0.113 | $i_l$ |
| $p_{14}$ | 1/cm | 7.7 | 21.3 | 13.2 | 23.2 | 20.0 | $C_a^*/T_i$ |
| $p_{15}$ | 1/second | $-6.7 \times 10^{-5}$ | $-2.5 \times 10^{-5}$ | $-4.5 \times 10^{-5}$ | $-2.1 \times 10^{-5}$ | $-2.7 \times 10^{-5}$ | $k_2C_l/T_i$ |

TABLE 7

| Parameter | Unit | Individual judgment standards | Example 14 | Example 15 | Example 16 | Example 17 | Example 18 |
|---|---|---|---|---|---|---|---|
| $p_{11}$ | mA/cm² | 0.20-0.38 | outside the range | outside the range | within the range | within the range | within the range |
| $p_{12}$ | mA/cm² | 0.35-0.46 | outside the range | outside the range | within the range | within the range | within the range |
| $p_{13}$ | mA/cm² | 0.05-0.12 | outside the range | within the range | within the range | within the range | within the range |
| $p_{14}$ | 1/cm | 10.0-30.0 | outside the range | within the range | within the range | within the range | within the range |
| $p_{15}$ | 1/second | $-5.0 \times 10^{-5}$ – $-1.5 \times 10^{-5}$ | outside the range | within the range | within the range | within the range | within the range |
| | | Judgment Result of analysis | bad | bad | good | good | good |
| | | Judgment Result of measurement | bad | bad | good | good | good |

Examples 19 to 23

In Examples 19 to 23, the subsamples 3-3, 4-3, 5-3, 6-3 and 7-3 were, respectively, analyzed by use of an electrolytic copper plating solution analyzer 110.

The conditions of the working electrode 18, reference electrode 19 and counter electrode 21 and the measurement conditions of the potential were the same as those of Example 1.

Among the measurement data, potential data within a range of 50 seconds to 1200 seconds in elapsed time t were used to analyze the condition of the subsamples 3-3, 4-3, 5-3, 6-3 and 7-3 by means of an analysis unit 131.

The parameters $p_{21}$ to $p_{23}$ calculated by the analysis unit 131 and the results of judgment of the condition of the plating solutions are shown in Tables 8 and 9, respectively. The units of the parameters $p_{21}$, $p_{22}$ are both mA/cm² and the unit of $p_{23}$ is 1/cm.

TABLE 8

| Parameter | Unit | Example 19 | Example 20 | Example 21 | Example 22 | Example 23 | Remarks |
|---|---|---|---|---|---|---|---|
| $p_{21}$ | mA/cm² | 0.044 | 0.024 | 0.021 | 0.020 | 0.025 | $i_i$ |
| $p_{22}$ | mA/cm² | 0.096 | 0.108 | 0.092 | 0.111 | 0.105 | $i_a$ |
| $p_{23}$ | 1/cm | 14.0 | 24.5 | 17.5 | 24.9 | 23.1 | $C_a^*/T_i$ |

TABLE 9

| Parameter | Unit | Individual judgment standards | Example 19 | Example 20 | Example 21 | Example 22 | Example 23 |
|---|---|---|---|---|---|---|---|
| $p_{21}$ | mA/cm² | 0.015-0.023 | outside the range | outside the range | within the range | within the range | outside the range |
| $p_{22}$ | mA/cm² | 0.08-0.20 | within the range | within the range | within the range | within the range | within the range |
| $p_{23}$ | 1/cm | 15.0-30.0 | outside the range | outside the range | within the range | within the range | within the range |
| | | Judgment result of analysis | bad | bad | good | good | good |
| | | Judgment result of measurement | bad | bad | good | good | good |

Examples 24 to 28

In Examples 24 to 28, the subsamples 3-4, 4-4, 5-4, 6-4 and 7-4 were, respectively, analyzed by use of an electrolytic copper plating solution analyzer 160. The conditions of the working electrode 18, reference electrode 19 and counter electrode 21 and the measurement conditions of the potential were the same as those of Example 1.

Among the measurement data, potential data within a range of 200 seconds to 1200 seconds in elapsed time t were used to analyze the condition of the subsamples 3-4, 4-4, 5-4, 6-4 and 7-4 by means of an analysis unit 181.

The parameters $p_{31}$, $p_{32}$ calculated by the analysis unit 181 and the results of judgment of the condition of the plating solutions are shown in Tables 10, 11, respectively. In the tables, the units of the parameter $p_{31}$ is mA/cm² and the unit of $p_{32}$ is 1/cm.

TABLE 10

| Parameter | Unit | Example 24 | Example 25 | Example 26 | Example 27 | Example 28 | Remarks |
|---|---|---|---|---|---|---|---|
| $p_{31}$ | mA/cm² | 0.095 | 0.108 | 0.091 | 0.111 | 0.105 | $i_a$ |
| $p_{32}$ | 1/cm | 19.9 | 33.1 | 21.6 | 33.5 | 30.6 | $C_a^*/T_i$ |

TABLE 11

| Parameter | Unit | Individual judgment standards | Example 24 | Example 25 | Example 26 | Example 27 | Example 28 |
|---|---|---|---|---|---|---|---|
| $p_{31}$ | mA/cm² | 0.090-0.106 | within the range | outside the range | within the range | outside the range | within the range |

TABLE 11-continued

| Parameter | Unit | Individual judgment standards | Example 24 | Example 25 | Example 26 | Example 27 | Example 28 |
|---|---|---|---|---|---|---|---|
| $p_{32}$ | 1/cm | 21.0-35.0 | outside the range | within the range | within the range | within the range | within the range |
| | | Judgment Result of analysis | bad | bad | good | bad | good |
| | | Judgment result of measurement | bad | bad | good | good | good |

<Judgment of the Condition of the Plating Solutions>

In Examples 9 to 13, the parameters $p_1$ to $p_5$ were identified, and whether the condition of a plating solution serving as an analysis object is "good" or "bad" were judged in view of the combination of the parameters $p_1$ to $p_5$. Accordingly, an individual judgment standard, with which the condition of a plating solution serving as an analysis object is judged as "good", were provided for each of the parameters $p_1$ to $p_5$. Moreover, as the judgment standard based on the combination of the parameters $p_1$ to $p_5$, the condition of a plating solution was judged as "good" only when the plating solution was "good" for all the individual judgment standards of the parameters $p_1$ to $p_5$. In other words, if one or more of the parameters $p_1$ to $p_5$ did not satisfy the individual judgment standard, the condition of such a plating solution was judged as "bad". It is to be understood that 'good" and "bad" are relative terms for purposes of this discussion.

As shown in Table 5, the range of "good" in the individual judgment standard for parameter $p_1$ was set at not less than 1.5 mA/cm² to not larger than 4.0 mA/cm².

The range of "good" in the individual judgment standard for parameter $p_2$ was set at not less than 0.08 mA/cm² to not larger than 0.2 mA/cm².

The range of "good" in the individual judgment standard for parameter $p_3$ was set at not less than 0.07 mA/cm² to not larger than 0.15 mA/cm².

The range of "good" in the individual judgment standard for parameter $p_4$ was set at not less than 20.0/cm to not larger than 60.0/cm.

The range of "good" in the individual judgment standard for parameter $p_5$ was set at not less than 0.01/second to not larger than 0.1/second.

In Table 5, the evaluation "as within the range" or "outside the range" is indicated based on the individual judgment in each example. Additionally, the evaluation as "good" or "bad" based on the results of the judgment for the combination is indicated at the column of "Judgment result of analysis".

The "good" or "bad" indicated at the column of "Judgment result of measurement" is a result of judgment of via-hole filling characteristics based on a measurement preliminarily obtained for every sample.

In Examples 14 to 18, the parameters $p_{11}$ to $p_{15}$ were identified, and whether the condition of a plating solution as an analysis object is "good" or "bad" was judged in view of the combination of the parameters $p_{11}$ to $p_{15}$. Accordingly, an individual judgment standard for each of the parameters $p_{11}$ to $p_{15}$ is provided to judge a plating solution, serving as an analysis object, as "good". Moreover, as a judgment standard for the combination of the parameters $p_{11}$ to $p_{15}$, only when all the individual judgment standards of the parameters $p_{11}$ to $p_{15}$ were "good", the condition of the plating solution was judged as "good". More particularly, if one or more of the parameters $p_{11}$ to $p_{15}$ did not satisfy their own individual judgment standard, the condition of the plating solution was judged as "bad".

As shown in Table 7, the range of "good" in the individual judgment standard of the parameter $p_{11}$ was set at not less than 0.20 mA/cm² to not larger than 0.38 mA/cm².

The range of "good" in the individual judgment standard of the parameter $p_{12}$ was set at not less than 0.35 mA/cm² to not larger than 0.46 mA/cm².

The range of "good" in the individual judgment standard of the parameter $p_{13}$ was set at not less than 0.07 mA/cm² to not larger than 0.12 mA/cm².

The range of "good" in the individual judgment standard of the parameter $p_{14}$ was set at not less than 10.0/cm to not larger than 30.0/cm.

The range of "good" in the individual judgment standard of the parameter $p_{15}$ was set at not less than $-5.0\times10^{-5}$/second to not larger than $-1.5\times10^{-5}$/second.

In Table 7, the evaluation is indicated as "within the range" or "outside the range" for the individual judgment standard in each example. The evaluation on "good" or "bad" based on the judgment of the combination is indicated at the column of "Judgment result of analysis".

The "good" or "bad" indicated at the column of "Judgment result of measurement" is a result of judgment of via-hole filling characteristics based on the measurement preliminarily obtained for every sample.

In Examples 19 to 23, the parameters $p_{21}$ to $p_{23}$ were identified, and whether the condition of a plating solution as an analysis object is "good" or "bad" was judged in view of the combination of the parameters $p_{21}$ to $p_{23}$. Accordingly, an individual judgment standard for each of the parameters $p_{21}$ to $p_{23}$ is provided to judge a plating solution, serving as an analysis object, as being "good". Moreover, as a judgment standard for the combination of the parameters $p_{21}$ to $p_{23}$, only when all the individual judgment standards of the parameters $p_{21}$ to $p_{23}$ were "good", the condition of the plating solution was judged as "good". More particularly, if one or more of the parameters $p_{21}$ to $p_{23}$ did not satisfy their own individual judgment standard, the condition of the plating solution was judged as "bad".

As shown in Table 9, the range of "good" in the individual judgment standard of the parameter $p_{21}$ was set at not less than 0.015 mA/cm² to not larger than 0.023 mA/cm².

The range of "good" in the individual judgment standard of the parameter $p_{22}$ was set at not less than 0.08 mA/cm² to not larger than 0.20 mA/cm².

The range of "good" in the individual judgment standard of the parameter $p_{33}$ was set at not less than 15.0/cm to not larger than 30.0/cm.

In Table 9, the evaluation is indicated as "within the range" or "outside the range" for the individual judgment standard in each example. The evaluation on "good" or "bad" based on the judgment of the combination is indicated at the column of "Judgment result of analysis".

The "good" or "bad" indicated at the column of "Judgment result of measurement" is a result of judgment of via-hole filling characteristics based on the measurement preliminarily obtained for every sample.

In Examples 24 to 28, the parameters $p_{31}$, $p_{32}$ were identified, and whether the condition of a plating solution as an analysis object is "good" or "bad" was judged in view of the combination of the parameters $p_{31}$, $p_{32}$. Accordingly, an individual judgment standard for each of the parameters $p_{31}$, $p_{32}$ is provided to judge a plating solution, serving as an analysis object, as being "good". Moreover, as a judgment standard for the combination of the parameters $p_{31}$, $p_{32}$, only when both the individual judgment standards of the parameters $p_{31}$, $p_{32}$ were "good", the condition of the plating solution was judged as "good". In other words, if one or both of the parameters $p_{31}$, $p_{32}$ did not satisfy their own individual judgment standard, the condition of the plating solution was judged as "bad".

As shown in Table 11, the range of "good" in the individual judgment standard of the parameter $p_{31}$ was set at not less than 0.090 mA/cm$^2$ to not larger than 0.106 mA/cm$^2$.

The range of "good" in the individual judgment standard of the parameter $p_{32}$ was set at not less than 21.0/cm to not larger than 35.0/cm.

In Table 11, the evaluation is indicated as "within the range" or "outside the range" for the individual judgment standard in each example. The evaluation on "good" or "bad" based on the judgment of the combination is indicated at the column of "Judgment result of analysis".

The "good" or "bad" indicated at the column of "Judgment result of measurement" is a result of judgment of via-hole filling characteristics based on the measurement preliminarily obtained for every sample.

<Discussion of the Results of the Judgment>

According to Table 5, the results of the analysis judgment in Examples 9 to 13 are coincident with the results of the measurement judgment. Accordingly, according to Examples 9 to 13, the identification of the parameters $p_1$ to $p_5$ enables the case that the condition of a plating solution is "good" and the case that the condition of a plating solution is "bad" to be differentiated from each other.

According to Table 7, the results of the analysis judgment of Examples 14 to 18 are coincident with those of the measurement judgment. Accordingly, according to Example 14 to 18, the identification of the parameters $p_{11}$ to $p_{15}$ enables the case that the condition of a plating solution is "good" and the case that the condition of a plating solution is "bad" to be differentiated from each other.

According to Table 9, the results of the analysis judgment in Examples 19 to 23 are such that the results of the analysis judgment are coincident with those of the measurement analysis in Examples 19 to 22, but are not coincident with those of the measurement judgment in Example 23. In Example 23, the plating solution in "good" condition was erroneously judged as "bad".

According to Table 11, the results of the analysis judgment in Examples 24 to 28 are such that the results are coincident with those results of the measurement judgment in Examples 24, 25, 26, 28, but not coincident with the results of the measurement judgment in Example 27. In Example 27, the plating solution in "good" condition was erroneously judged as "bad".

In this way, the parameters are identified in Examples 19 to 28 based on such a reaction mechanism that no consideration is taken to a leveler, the condition of a plating solution cannot be identified accurately.

Nevertheless, since a plating solution in bad condition is erroneously judged as "good", safety evaluation is made.

INDUSTRIAL APPLICABILITY

The present invention can be applicable to an electrolytic copper plating solution analyzer, or an analyzer for an electrolytic copper plating solution that is used for an electrolytic copper plating solution employed in a diversity of fields of ornament, copper foil fabrication, electronic parts and the like and is particularly used for an electrolytic copper plating solution which is employed for forming via holes (contact holes) formed in high density printed circuit boards, substrates for semiconductor package and semiconductor substrates, or employed for forming a conductor in a via hole, and also to a method of analyzing an electrolytic copper plating solution.

REFERENCE SIGNS LIST 10, 60, 110, 160 electrolytic copper plating solution analyzer
11 stand
11A stage unit
12 analysis container
13 electrolytic copper plating solution
18 working electrode
19 reference electrode
21 counter electrode
23 rotation drive unit
25 controller
26 current generation unit
28 potential measurement unit
31, 81, 131, 181 analysis unit
35 exterior member
35a tip end face (tip end of the exterior member)
35A working electrode body accommodation portion (recess at a central portion of the tip end face)
37 working electrode body
37a surface (the surface of the working electrode)
39 conductive wire
42, 92, 142, 192 analysis unit body
43 display
44 keyboard
t elapsed time
η potential.

What is claimed is:
1. An electrolytic copper plating solution analyzer, comprising:
an analysis container for accommodating, as an analysis sample, a part of an electrolytic copper plating solution containing additives serving as a promoter and an inhibitor;
a working electrode immersed in the electrolytic copper plating solution accommodated in the analysis container, the working electrode being capable of receiving and transferring electrons;
a reference electrode immersed in the electrolytic copper plating solution accommodated in the analysis container and used as a reference when a potential of the working electrode is determined;
a counter electrode immersed in the electrolytic copper plating solution accommodated in the analysis container;

a rotation drive unit capable of rotating the working electrode at a given speed;

a current generation unit capable of passing an electric current with a given current density between the working electrode and the counter electrode;

a potential meter for measuring a potential between the working electrode and the reference electrode; and a computer programmed to analyze a relation between an elapsed time after passage of the current and the potential, when the relation between the elapsed time and the potential is analyzed, calculate parameters indicating a condition of the electrolytic copper plating solution based on a reaction mechanism when a Cu(I) species, the Cu(I) species being generated on a surface of the working electrode during a deposition reaction of a copper plated film and that is formed from a component of the promoter and a Cu(I) ion, is substituted for the inhibitor, the inhibitor being located on the surface of the working electrode, and when the Cu(I) species forms a complex at least with the promoter; and identify the condition of the electrolytic copper plating solution from the calculated parameters, wherein the computer is programmed to analyze the relation between the elapsed time and the potential, measured with the potential meter, based on the following equations (41) and (61) to (63) to calculate, as the parameters, $i_i$, $i_a$, and $C_a^*/T_i$ $$\eta = A \cdot T\left[\ln\left\{\frac{i_i}{I}\exp\left(-B \cdot I\frac{C_a^*}{T_i}t\right) + \frac{i_a}{I}\left\{1 - \exp\left(-B \cdot I\frac{C_a^*}{T_i}t\right)\right\}\right\}\right] \quad (41)$$

$$A = \frac{R}{\alpha F} \quad (61)$$

$$B = \frac{1}{nFd} \quad (62)$$

$$C_a^* = \frac{kC_a}{BI} \quad (63)$$

wherein $\eta$ is the potential indicated above, T is a given temperature, I is the given current density, t is the elapsed time, $i_i$ is an exchange current density at a time of the deposition reaction of the copper plated film in a presence of the inhibitor, $i_a$ is an exchange current density at the time of deposition reaction of the copper plated film in a presence of the Cu(I) species, $C_a$ is a concentration of the promoter in the solution, $T_i$ is a saturation coverage of the inhibitor on a surface of the copper plated film, k is a reaction rate at which the inhibitor is substituted with the Cu(I) species with time due to a difference in adsorption rate therebetween, R is a universal gas constant, $\alpha$ is a transfer coefficient, F is the Faraday constant, d is a molar density of copper, and n is the valance of copper of the copper plated film.

2. An electrolytic copper plating solution analyzer, comprising:

an analysis container for accommodating, as an analysis sample, a part of an electrolytic copper plating solution containing additives serving as a promoter and an inhibitor;

a working electrode immersed in the electrolytic copper plating solution accommodated in the analysis container, the working electrode being capable of receiving and transferring electrons;

a reference electrode immersed in the electrolytic copper plating solution accommodated in the analysis container and used as a reference when a potential of the working electrode is determined;

a counter electrode immersed in the electrolytic copper plating solution accommodated in the analysis container;

a rotation drive unit capable of rotating the working electrode at a given speed;

a current generation unit capable of passing an electric current with a given current density between the working electrode and the counter electrode;

a potential meter for measuring a potential between the working electrode and the reference electrode; and a computer programmed to analyze a relation between an elapsed time after passage of the current and the potential, when the relation between the elapsed time and the potential is analyzed, calculate parameters indicating a condition of the electrolytic copper plating solution based on a reaction mechanism when a Cu(I) species, the Cu(I) species being generated on a surface of the working electrode during a deposition reaction of a copper plated film and that is formed from a component of the promoter and a Cu(I) ion, is substituted for the inhibitor, the inhibitor being located on the surface of the working electrode, and when the Cu(I) species forms a complex at least with the promoter; and identify the condition of the electrolytic copper plating solution from the calculated parameters, wherein the computer is programmed to analyze the relation between the elapsed time and the potential measured with the potential meter based on the following equations (42) and (64) to (66) to calculate $i_a$ and $C_a^*/T_i$ as the parameters $$\eta = A \cdot T\left[\ln\left(\frac{i_a}{I}\right) + \ln\left\{1 - \exp\left(-B \cdot I\frac{C_a^*}{T_i}t\right)\right\}\right] \quad (42)$$

$$A = \frac{R}{\alpha F} \quad (64)$$

$$B = \frac{1}{nFd} \quad (65)$$

$$C_a^* = \frac{kC_a}{BI} \quad (66)$$

wherein $\eta$ is the potential indicated above, T is a given temperature, I is the given current density, t is the elapsed time, $i_a$ is an exchange current density at a time of deposition reaction of the copper plated film in a presence of the Cu(I) species, $C_a$ is a concentration of the promoter in the solution, $T_i$ is a saturation coverage of the inhibitor on a surface of the copper plated film, k is a reaction rate at which the inhibitor is substituted with the Cu(I) species with time due to a difference in adsorption rate therebetween, R is a universal gas constant, $\alpha$ is a transfer coefficient, F is the Faraday constant, d is a molar density of copper, and n is the valance of copper of the copper plated film.

3. A method for analyzing an electrolytic copper plating solution, comprising:

immersing a working electrode, a reference electrode, and a counter electrode in an electrolytic copper plating solution that is kept at a given temperature and contains additives including a promoter, an inhibitor, and a leveler, and rotating the working electrode at a given speed;

passing an electric current with a given current density between the working electrode and the counter electrode to measure a potential between the working electrode and the reference electrode; and analyzing a relation between an elapsed time after the current passage and the potential, wherein parameters indicating a condition of the electrolytic copper plating solution are calculated based on a reaction mechanism when a Cu(I) species generated on a surface of the working electrode during a deposition reaction of a copper plated film and is formed from a component of the promoter and a Cu(I) ion, is substituted for the inhibitor, the inhibitor being located on the surface of the working electrode, as the deposition reaction of the copper plated film proceeds, the leveler is substituted for the Cu(I) species located on the surface of the working electrode, as the deposition reaction of the copper plated film proceeds, and the Cu(I) species forms a complex at least with the promoter; and identifying by a computer, the condition of the electrolytic copper plating solution using the parameters, wherein the relation between the elapsed time after the passage of the current and the potential is analyzed based on the following equations (1) to (4) to calculate $i_i$, $i_a$, $i_l$, $C_a^*/T_i$ and $k_2 \cdot C_l/T_i$ as the parameters $$\eta = AT \cdot \ln\left[\frac{i_i}{I} \cdot \exp\left(-BI\frac{C_a^*}{T_i}t\right) + \frac{i_a}{I}\left\{1 - \exp\left(-BI\frac{C_a^*}{T_i}t\right)\right\} + \frac{i_l - i_a}{I} \cdot \exp\left(-\frac{k_2 C_l}{T_i}t\right)\right] \quad (1)$$

$$A = \frac{R}{\alpha F} \quad (2)$$

$$B = \frac{1}{nFd} \quad (3)$$

$$C_a^* = \frac{kC_a}{BI} \quad (4)$$

wherein η is the potential indicated above, T is the given temperature indicated above, I is the current density, t is the elapsed time, $i_i$ is an exchange given current density at the time of deposition reaction of the copper plated film in a presence of the inhibitor, $i_a$ is an exchange current density at the time of deposition reaction of the copper plated film in a presence of the Cu(I) species, ii is an exchange current density at the time of deposition reaction of the copper plated film in the presence of the leveler, $C_a$ is a concentration of the promoter in the solution, $C_l$ is a concentration of the leveler in the solution, $T_i$ is a saturation coverage of the inhibitor on a surface of the copper plated film, k is a reaction rate at which the inhibitor is substituted with the Cu(I) species with time due to a difference in adsorption rate therebetween, $k_2$ is a reaction rate at which the Cu(I) species is substituted with the leveler with time due to the difference in adsorption rate therebetween, R is a universal gas constant, α is a transfer coefficient, F is the Faraday constant, d is a molar density of copper, and n is the valance of copper of the copper plated film.

4. A method for analyzing an electrolytic copper plating solution, comprising:

immersing a working electrode, a reference electrode, and a counter electrode in an electrolytic copper plating solution that is kept at a given temperature and contains additives including a promoter, an inhibitor, and a leveler, and rotating the working electrode at a given speed;

passing an electric current with a given current density between the working electrode and the counter electrode to measure a potential between the working electrode and the reference electrode; and analyzing a relation between an elapsed time after the current passage and the potential, wherein parameters indicating a condition of the electrolytic copper plating solution are calculated based on a reaction mechanism when a Cu(I) species generated on a surface of the working electrode during a deposition reaction of a copper plated film and is formed from a component of the promoter and a Cu(I) ion, is substituted for the inhibitor, the inhibitor being located on the surface of the working electrode, as the deposition reaction of the copper plated film proceeds, the leveler is substituted for the Cu(I) species located on the surface of the working electrode, as the deposition reaction of the copper plated film proceeds, and the Cu(I) species forms a complex at least with the promoter; and identifying by a computer, the condition of the electrolytic copper plating solution using the parameters, wherein the relation between the time elapsed after the passage of the current and the potential is analyzed based on the following equations (5) to (8) to calculate $i_i$, $i_a$, $i_l$, $C_a^*/T_i$ and $k_3 \cdot C_l/T_i$ as the parameters $$\eta = AT \cdot \ln\left[\frac{i_i}{I} \cdot \exp\left(-BI\frac{C_a^*}{T_i}t\right) + \frac{i_a}{I}\left\{1 - \exp\left(-BI\frac{C_a^*}{T_i}t\right)\right\} + \frac{i_l - i_a}{I} \cdot \exp\left(-\frac{k_3 C_l}{T_i}t\right)\right] \quad (5)$$

$$A = \frac{R}{\alpha F} \quad (6)$$

$$B = \frac{1}{nFd} \quad (7)$$

$$C_a^* = \frac{kC_a}{BI} \quad (8)$$

wherein η is the potential indicated above, T is the given temperature indicated above, I is the current density, t is the elapsed time, $i_i$ is an exchange given current density at the time of deposition reaction of the copper plated film in a presence of the inhibitor, $i_a$ is an exchange current density at the time of deposition reaction of the copper plated film in a presence of the Cu(I) species, ii is an exchange current density at the time of the deposition reaction of the copper plated film in the presence of the leveler, $C_a$ is a concentration of the promoter in the solution bulk, $C_l$ is a concentration of the leveler in the solution, $T_i$ is a saturation coverage of the inhibitor on a surface of the copper plated film, k is a reaction rate at which the inhibitor is substituted with the Cu(I) species with time due to a difference in adsorption rate therebetween, $k_3$ is a reaction rate at which the inhibitor is substituted with the leveler with time due to a difference in adsorption rate therebetween, R is a universal gas constant, α is a transfer coefficient, F is the Faraday constant, d is a molar density of copper, and n is the valance of copper of the copper plated film.

5. A method for analyzing an electrolytic copper plating solution, comprising:
immersing a working electrode, a reference electrode and a counter electrode in an electrolytic copper plating solution that contains additives including a promoter and an inhibitor, and rotating the working electrode at a given speed, wherein the electrolytic copper plating solution is used in a plating apparatus and is kept at a given temperature;
passing an electric current with a given current density between the working electrode and the counter electrode to measure a potential between the working electrode and the reference electrode; and
analyzing a relation between an elapsed time after passage of the current and the potential,
wherein parameters indicating a condition of the electrolytic copper plating solution are calculated based on a reaction mechanism when a Cu(I) species generated on a surface of the working electrode during a deposition reaction of a copper plated film is substituted for the inhibitor, the inhibitor being located on the surface of the working electrode, as the deposition reaction of the copper plated film proceeds, and the Cu(I) species forms a complex at least with the promoter; and
identifying, by a computer, the condition of the electrolytic copper plating solution using the parameters,
wherein the relation between the elapsed time after the current passage and the potential is analyzed based on the following equations (41), (61) to (63) to calculate $i_i$, $i_a$ and $C_a^*/T_i$ as the parameters $$\eta = A \cdot T\left[\ln\left\{\frac{i_i}{I}\exp\left(-B \cdot I\frac{C_a^*}{T_i}t\right) + \frac{i_a}{I}\left\{1 - \exp\left(-B \cdot I\frac{C_a^*}{T_i}t\right)\right\}\right\}\right] \quad (41)$$

$$A = \frac{R}{\alpha F} \quad (61)$$

$$B = \frac{1}{nFd} \quad (62)$$

$$C_a^* = \frac{kC_a}{BI} \quad (63)$$

wherein η is the potential indicated above, T is a given temperature indicated above, I is the given current density, t is the elapsed time, $i_i$ is an exchange current density at the time of deposition reaction of the copper plated film in a presence of the inhibitor, $i_a$ is an exchange current density at a time of the deposition reaction of the copper plated film in a presence of the Cu(I) species, $C_a$ is a concentration of the promoter in the solution, $T_i$ is a saturation coverage of the inhibitor on the surface of the copper plated film, k is a reaction rate at which the inhibitor is substituted with the Cu(I) species with time due to a difference in adsorption rate therebetween, R is a universal gas constant, a is a transfer coefficient, F is the Faraday constant, d is a molar density of copper, and n is the valance of copper of the copper plated film.

6. A method for analyzing an electrolytic copper plating solution, comprising:
immersing a working electrode, a reference electrode and a counter electrode in an electrolytic copper plating solution that contains additives including a promoter and an inhibitor, and rotating the working electrode at a given speed, wherein the electrolytic copper plating solution is used in a plating apparatus and is kept at a given temperature;
passing an electric current with a given current density between the working electrode and the counter electrode to measure a potential between the working electrode and the reference electrode; and
analyzing a relation between an elapsed time after passage of the current and the potential,
wherein parameters indicating a condition of the electrolytic copper plating solution are calculated based on a reaction mechanism when a Cu(I) species generated on a surface of the working electrode during a deposition reaction of a copper plated film is substituted for the inhibitor, the inhibitor being located on the surface of the working electrode, as the deposition reaction of the copper plated film proceeds, and the Cu(I) species forms a complex at least with the promoter; and
identifying, by a computer, the condition of the electrolytic copper plating solution using the parameters,
wherein the relation between the elapsed time after the current passage and the potential is analyzed based on the following equations (42) and (64) to (66) to calculate $i_a$ and $C_a^*/T_i$ as the parameters $$\eta = A \cdot T\left[\ln\left(\frac{i_a}{I}\right) + \ln\left\{1 - \exp\left(-B \cdot I\frac{C_a^*}{T_i}t\right)\right\}\right] \quad (42)$$

$$A = \frac{R}{\alpha F} \quad (64)$$

$$B = \frac{1}{nFd} \quad (65)$$

$$C_a^* = \frac{kC_a}{BI} \quad (66)$$

wherein η is the potential indicated above, T is a given temperature indicated above, I is the given current density, t is the elapsed time, $i_a$ is an exchange current density at the time of deposition reaction of the copper plated film in a presence of the Cu(I) species, $C_a$ is a concentration of the promoter in the solution, $T_i$ is a saturation coverage of the inhibitor on a surface of the copper plated film, k is a reaction rate at which the inhibitor is substituted with the Cu(I) species with time due to a difference in adsorption rate therebetween, R is a universal gas constant, a is a transfer coefficient, F is the Faraday constant, d is a molar density of copper, and n is the valance of copper of the copper plated film.

* * * * *